(12) United States Patent
Wach

(10) Patent No.: US 8,948,560 B1
(45) Date of Patent: Feb. 3, 2015

(54) ELEVATING NUMERICAL APERTURE OF OPTICAL SYSTEMS

(75) Inventor: Michael L. Wach, Alpharetta, GA (US)

(73) Assignee: Cirrex Systems, LLC, Wilmington, DE (US)

( * ) Notice: Subject to any disclaimer, the term of this patent is extended or adjusted under 35 U.S.C. 154(b) by 824 days.

(21) Appl. No.: 13/065,120

(22) Filed: Mar. 15, 2011

Related U.S. Application Data

(60) Provisional application No. 61/340,261, filed on Mar. 15, 2010, provisional application No. 61/343,736, filed on May 3, 2010.

(51) Int. Cl.
*G02B 6/032* (2006.01)
*G02B 6/04* (2006.01)
*G02B 6/00* (2006.01)

(52) U.S. Cl.
USPC ............. 385/125; 385/24; 385/115; 385/123; 385/131

(58) Field of Classification Search
None
See application file for complete search history.

(56) References Cited

U.S. PATENT DOCUMENTS

| | | | |
|---|---|---|---|
| 5,802,236 A | 9/1998 | DiGiovanni et al. | |
| 5,912,278 A | 6/1999 | Venkataraman | |
| 5,953,477 A | 9/1999 | Wach et al. | |
| 6,444,719 B1 | 9/2002 | Mizumoto et al. | |
| RE37,932 E | 12/2002 | Baldwin et al. | |
| 6,555,590 B1 | 4/2003 | Tan | |
| 6,580,935 B1 | 6/2003 | Wach et al. | |
| 6,593,384 B2 | 7/2003 | Anderson et al. | |
| 6,617,364 B2 | 9/2003 | Soane et al. | |
| 6,638,984 B2 | 10/2003 | Soane et al. | |
| 6,709,870 B2 | 3/2004 | Suzuki et al. | |
| 6,790,870 B1 | 9/2004 | DeSimone et al. | |
| 7,120,342 B2 | 10/2006 | Chang et al. | |
| 7,407,498 B2 | 8/2008 | Olson | |
| 7,585,557 B2 | 9/2009 | Aylward et al. | |
| 7,921,675 B2 * | 4/2011 | Bookbinder et al. | ............ 65/416 |
| 8,132,971 B2 * | 3/2012 | Luther et al. | .................... 385/83 |
| 2002/0071947 A1 | 6/2002 | Soane et al. | |
| 2002/0191928 A1 * | 12/2002 | Carter et al. | .................. 385/127 |

(Continued)

FOREIGN PATENT DOCUMENTS

WO  WO 2009-121055  10/2009

OTHER PUBLICATIONS

Town et al. ("Randomly Microstructured Polymer Optical Fibre", ACOFT/AOS 2006 Proceedings, Jul. 13, 2006, pp. 102-103).*

(Continued)

*Primary Examiner* — Michelle R Connelly
(74) *Attorney, Agent, or Firm* — Ascenda Law Group, PC

(57) ABSTRACT

An optical material can be formed by creating extremely small voids or gas-filled bubbles in a polymeric material, such as a thermoplastic or a fluoropolymer. The voids or gas-filled bubbles can reduce the refractive index of the optical material substantially below the polymeric material's refractive index. Dimensionally, the voids or gas-filled bubbles can be smaller than the wavelength of light that is intended to interact with the optical material, thereby avoiding undue scattering loss. The voids or gas-filled bubbles can be formed via adding particles of gas-generating material to the polymeric material and heating the resulting composition. The voids or gas-filled bubbles can form as the heat causes the polymeric material to melt and the particles to generate gas. The optical material can be utilized as a cladding to provide a high numerical aperture optical fiber, for example.

11 Claims, 13 Drawing Sheets

(56) References Cited

U.S. PATENT DOCUMENTS

| | | | |
|---|---|---|---|
| 2003/0008931 | A1 | 1/2003 | Soane et al. |
| 2005/0180710 | A1* | 8/2005 | Oh et al. ............... 385/125 |
| 2006/0067638 | A1 | 3/2006 | Chang et al. |
| 2007/0123598 | A1 | 5/2007 | Nam et al. |
| 2008/0085086 | A1* | 4/2008 | Herz et al. ............. 385/123 |
| 2008/0131066 | A1* | 6/2008 | Bickham et al. ....... 385/125 |
| 2009/0018225 | A1 | 1/2009 | Gemmel et al. |
| 2009/0032983 | A1* | 2/2009 | Bookbinder et al. ... 264/1.24 |
| 2009/0048359 | A1 | 2/2009 | Glew et al. |
| 2014/0013808 | A1* | 1/2014 | KIM et al. .............. 65/393 |

OTHER PUBLICATIONS

Seo et al., "Diffused Reflection of Microcellular Foamed Polycarbonate," Apr. 2009, *Polymer-Plastics Technology and Engineering*, 48(4): 351-358. Abstract only.

"Extrusion of Foamed Rigid PVC Dry Blend" downloaded as early as Mar. 15, 2011 from http://www.tramaco.de, 4 pp.

"Plain $SiO_2$ silica nanospheres and microspheres," downloaded May 19, 2009 from http://www.microspheres-nanospheres.com/Microspheres/Inorganic/Silica/SiO2%20Plain.htm, 6 pp.

Liang et al., "Pt Hollow Nanospheres: Facile Synthesis and Enhanced Electrocatalysts," 2004, *Angew. Chem. Int. Ed.*, 43:1540-1543.

Kloeppel, James, "High-intensity ultrasound creates hollow nanospheres and nanocrystals," Feb. 22, 2005, downloaded from http:news.bio-medicines.org/medicine-news-2/High-intensity-ultrasound-creates-hollow-nanosphers-and-nanocrystals-533-1/, 2 pp.

Berger, Michael, "Creating differently shaped and sized hollow nanospheres from a single template," Apr. 7, 2006, downloaded from http://www.nanowerk.com/spotlight/spotid=411.php.

"Glass nanospheres and microspheres," downloaded May 19, 2009 from http://www.microspheres-nanospheres.com/Microsodpheres/Inorganic/Glass/hollow%20glass%20beads.htm, 2 pp.

"Mknano", downloaded May 18, 2009 from http://www.mknano.com/, 3 pp.

Hu, Xianguo, "On the size effect of molybdenum disulfide particles on tribological performance," 2005, *Industrial Lubrication and Tribology*, 57(6):255-259. Abstract only.

\* cited by examiner

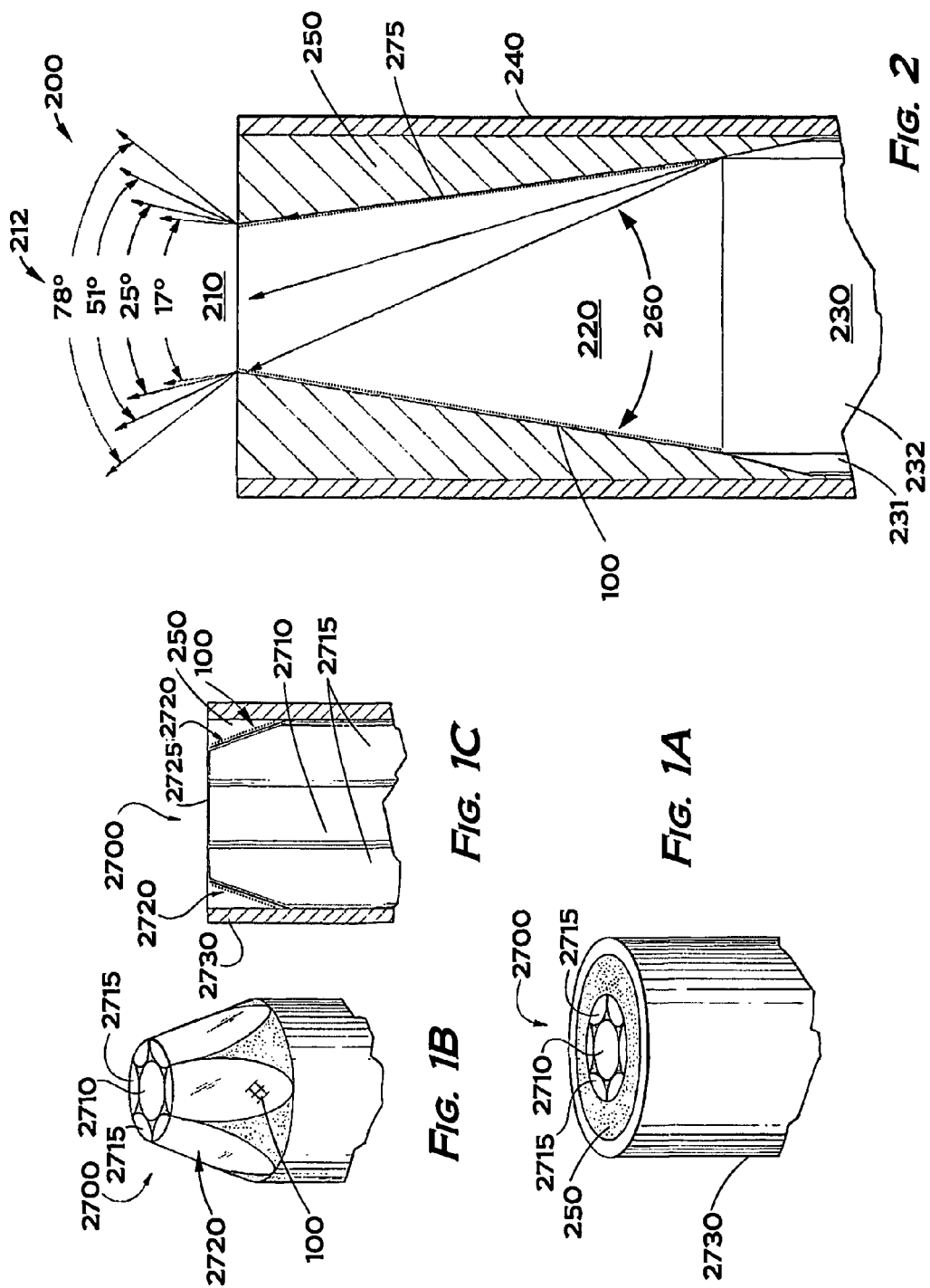

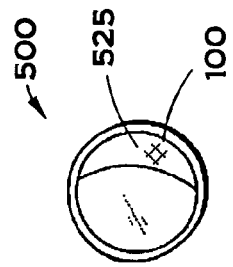
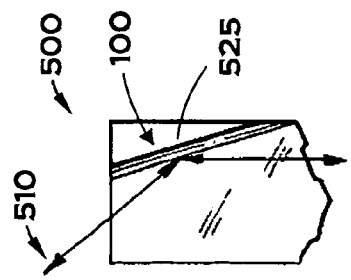
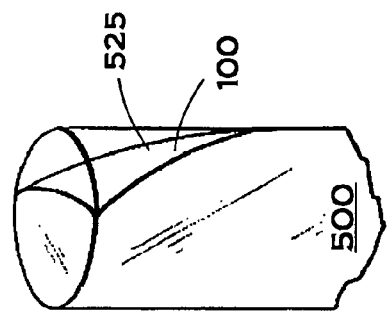
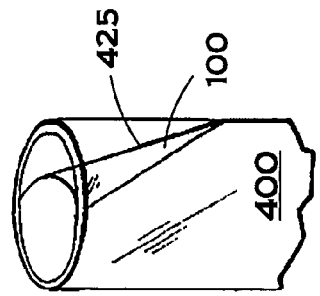
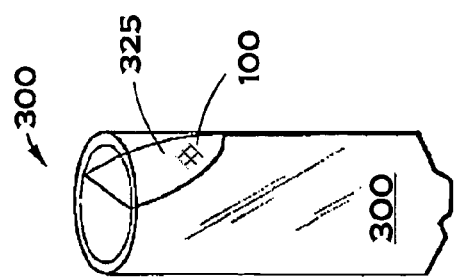
Fig. 5B
Fig. 5C
Fig. 5A
Fig. 4
Fig. 3

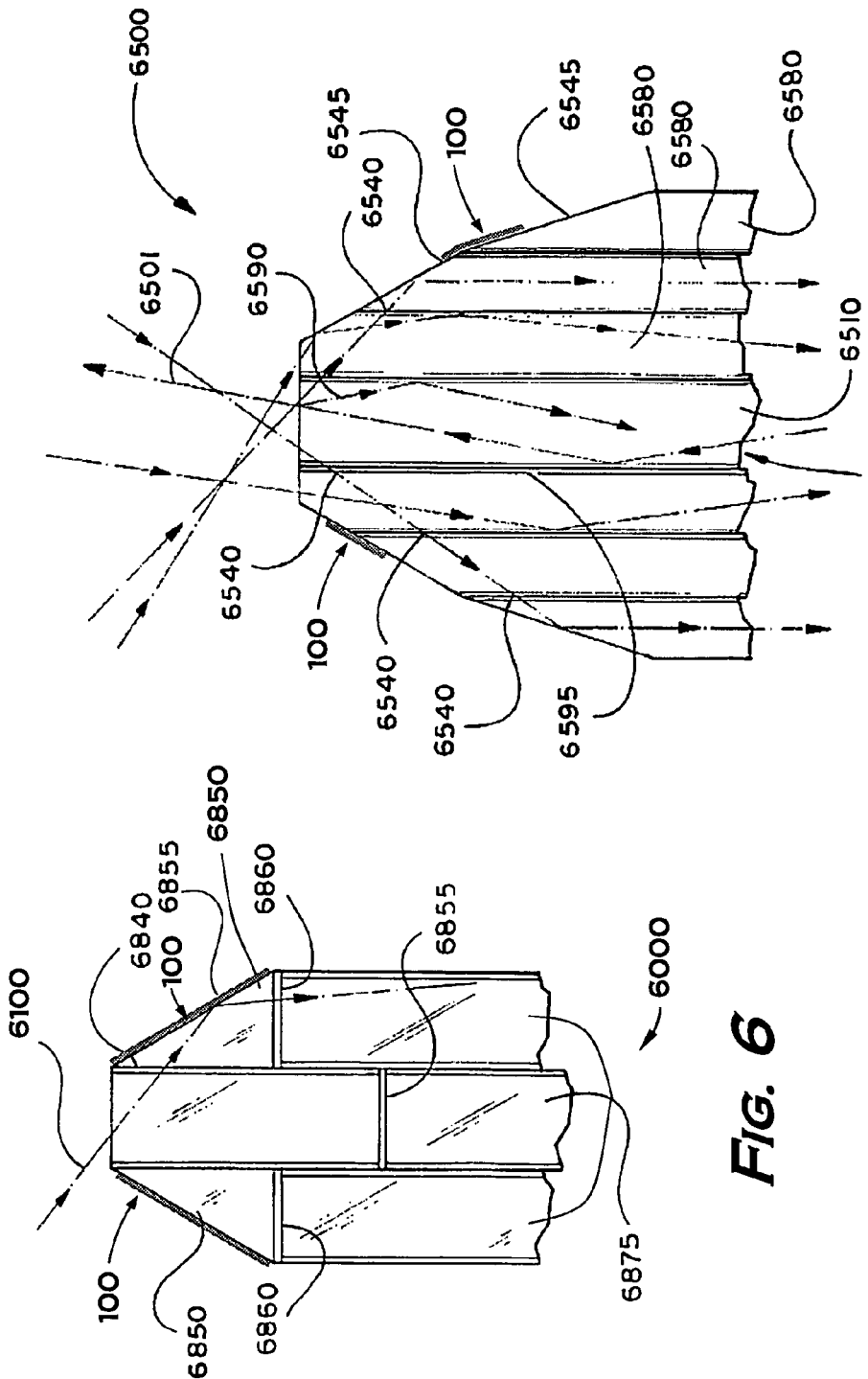

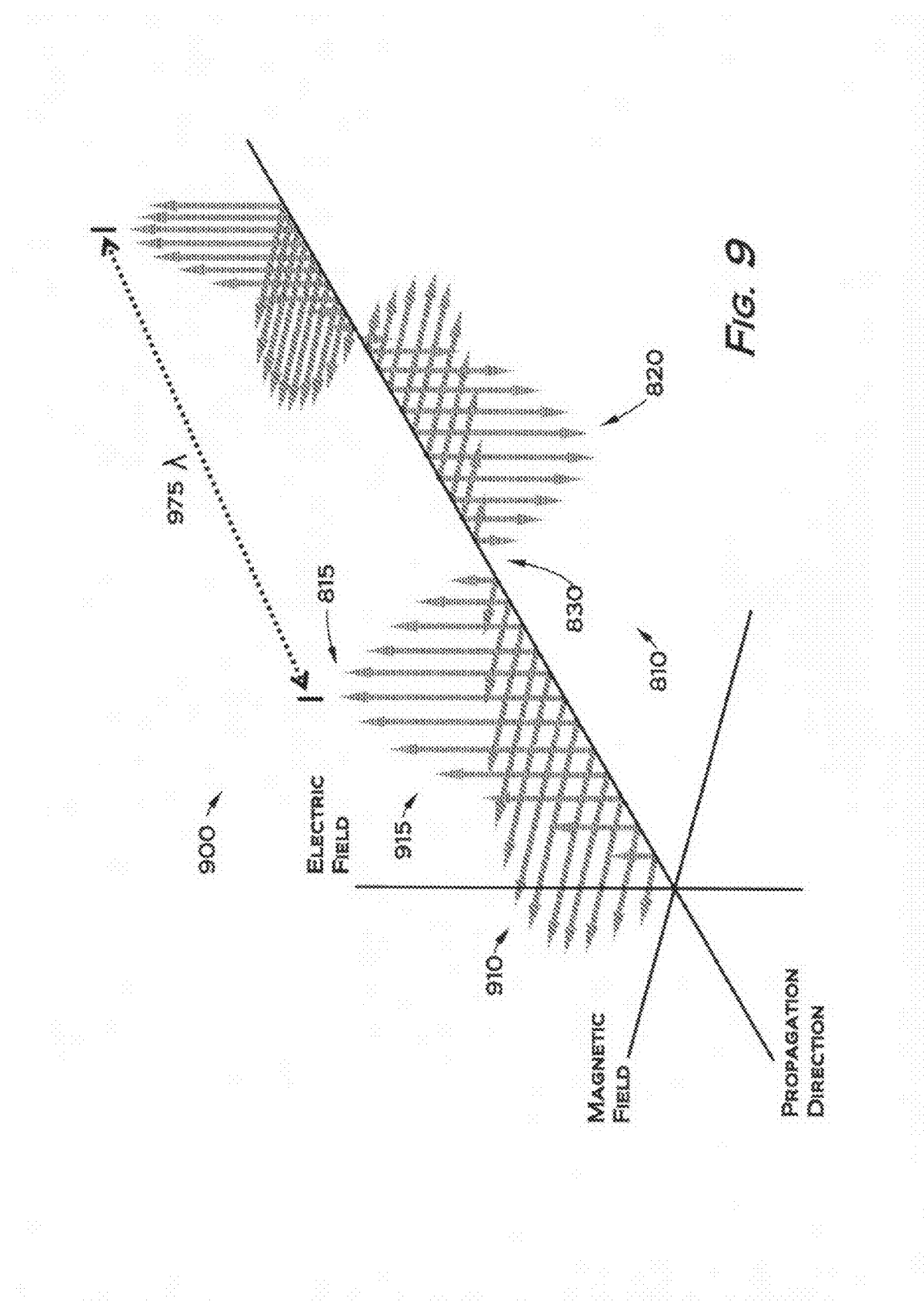

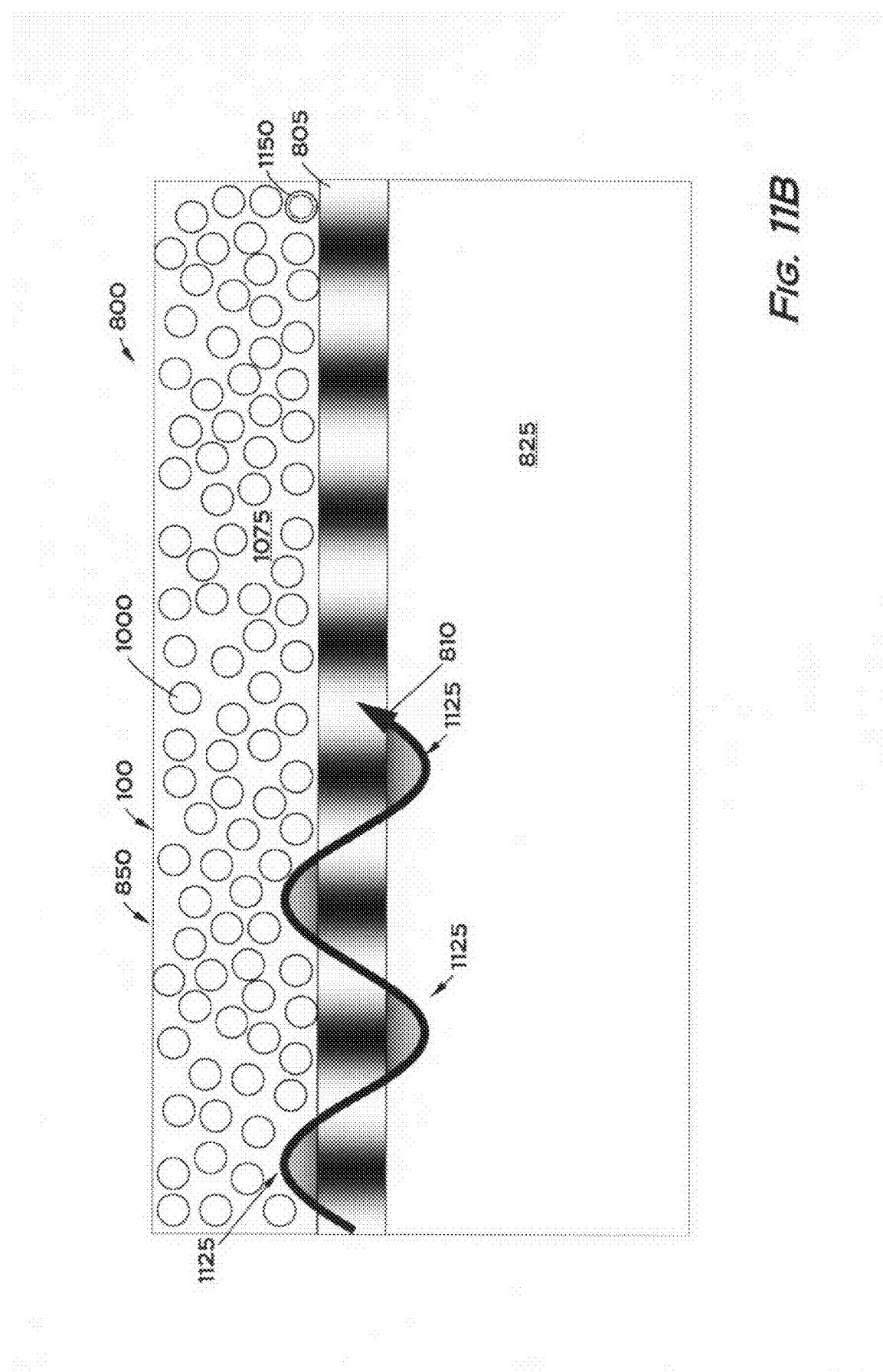

ELEVATING NUMERICAL APERTURE OF OPTICAL SYSTEMS

CROSS REFERENCE TO RELATED APPLICATIONS

This application claims priority to U.S. Provisional Patent Application No. 61/340,261 filed Mar. 15, 2010 in the name of Wach and entitled "Elevating Numerical Aperture of Optical Systems," the entire contents of which are hereby incorporated herein by reference. This application claims priority to U.S. Provisional Patent Application No. 61/343,736 filed May 3, 2010 in the name of Wach and entitled "Elevating Numerical Aperture of Optical Systems," the entire contents of which are hereby incorporated herein by reference.

TECHNICAL FIELD

The present technology relates generally to optical interfaces that can internally reflect light and materials for forming such interfaces, such as a fiber optic cladding adhering to a fiber optic core, and more specifically to optical coatings comprising polymeric material containing gas-filled bubbles dimensioned smaller than the internally reflected light's wavelength, whereby the bubbles reduce refractive index while avoiding undue scattering-related loss.

BACKGROUND

An optical waveguide can comprise two longitudinally extending materials with different refractive indices that adjoin or contact one another to form an optical interface running lengthwise. The interface can be internally reflective as a result of a refractive index differential between the two materials. The interface can reflect light propagating along the high-refractive index material that is incident upon the interface. For example, a multimode or single mode optical fiber can comprise a cladding and a core, with the cladding adjoining and/or circumferentially surrounding the core and having a lower refractive index than the core. Such a basic architecture can be adapted for numerous applications, like illumination systems, head-mounted surgery lights, light pipes, endoscopes, single-mode optical fibers, communication optical fibers, multimode optical fibers, fiber optic sensors, planar lightguide circuits ("PLCs," also known as "planar lightwave circuits"), and optical buses, to name a few examples.

In many instances, the refractive index differential between the two materials establishes, defines, influences, or sets light propagation characteristics of the optical waveguide. For example, an optical fiber's numerical aperture can be a function of the respective refractive indices of the fiber's core and cladding, with a high refractive index differential supporting a high numerical aperture. Thus, increasing the refractive index differential facilitates accepting, emitting, and/or transmitting light of greater angular orientation.

In many situations, silica, silicate, silicon dioxide, glass, or glassy material provides a desirable material for a core of an optical waveguide. Such a core can be coated with a polymer having a refractive index lower than that of the core to form a clad waveguide. However, conventional polymer-based cladding materials generally have a limited range of refractive indices, without supporting a refractive index that is as low as would be desirable for many applications. Accordingly, conventional waveguide technologies are often lacking in terms of receiving, guiding, and/or delivering light that is oriented at aggressive angles relative to an optical waveguide's longitudinal axis.

In view of the foregoing discussion of representative deficiencies in the art, need exists for improved optical materials and for improved optical waveguide and fiber optic technologies. Need exists for an optical material system having a refractive index that is low, that is flexible, and/or that can be adapted according to application. Need further exists for high numerical aperture optical fibers and optical waveguides. Need also exists for a technology that can substantially reduce the refractive index of an optical polymer, or other optical material, having otherwise desirable properties, such as desirable optical, mechanical, workability, coating, manufacturability, chemical, stability, or other properties. A technology addressing such a need, or some other related shortcoming in the art, would promote photonic and optical applications.

SUMMARY

The present invention supports adapting a material's refractive index to achieve an application goal and utilizing such a material to provide optical systems that can internally reflect light and/or guide light at relatively steep angles and/or under a desirable numerical aperture.

In one aspect of the present invention, an optical material is processed to form bubbles, cavities, cells, voids, gas-filled inclusions, pockets, or similar structures that are operative to reduce the material's refractive index. Such bubbles, cavities, cells, voids, gas-filled inclusions, pockets, or similar structures can be nanoscaled or dimensioned smaller than a wavelength of light that interacts with the material or that the material manages. In this manner, the material can have desirable scattering performance, for example avoiding deleterious levels of loss. The material can be combined with another optical material of higher refractive index to form an internally reflective interface as may be useful for waveguides and optical fibers as well as for other optical systems.

The discussion of optical materials and systems presented in this summary is for illustrative purposes only. Various aspects of the present invention may be more clearly understood and appreciated from a review of the following detailed description of the disclosed embodiments and by reference to the figures and claims. Other aspects, systems, processes, methods, features, advantages, benefits, and objects of the present invention will become apparent to one of ordinary skill in the art upon examination of the following detailed description and the accompanying figures. It is intended that all such aspects, systems, processes, methods, features, advantages, benefits, and objects are to be included within this description, are to be within the scope of the present invention, and are to be protected by the accompanying claims.

BRIEF DESCRIPTION OF THE FIGURES

FIGS. 1A, 1B, and 1C (collectively FIG. 1) are illustrations of a fiber optic system comprising an internally reflective surface formed at an interface between silica and an optical material comprising polymeric material and gas-filled bubbles in accordance with certain exemplary embodiments of the present invention.

FIG. 2 is an illustration of a fiber optic system comprising a tapered optical fiber, wherein the taper is coated with an optical material comprising polymeric material and gas-filled bubbles in accordance with certain exemplary embodiments of the present invention.

FIG. 3 is an illustration of an optical fiber having a beam manipulating feature that includes a coating of optical material exhibiting a low refractive index and comprising polymeric material and gas-filled bubbles in accordance with certain exemplary embodiments of the present invention.

FIG. 4 is an illustration of an optical fiber having a beam manipulating feature that includes a coating of optical material exhibiting a low refractive index and comprising polymeric material and gas-filled bubbles in accordance with certain exemplary embodiments of the present invention.

FIGS. 5A, 5B, and 5C (collectively FIG. 5) are illustrations of an optical fiber having a beam manipulating feature that includes an optical material exhibiting a low refractive index and comprising polymeric material and gas-filled bubbles in accordance with certain exemplary embodiments of the present invention.

FIG. 6 is an illustration of a fiber optic system comprising internally reflective surfaces formed at interfaces between silica and an optical material comprising polymeric material and gas-filled bubbles in accordance with certain exemplary embodiments of the present invention.

FIG. 7 is an illustration of a fiber optic system comprising an internally reflective surface formed at an interface between silica and an optical material comprising polymeric material and gas-filled bubbles in accordance with certain exemplary embodiments of the present invention.

FIG. 9 is an illustration of a plot of an electromagnetic wave of light in accordance with certain exemplary embodiments of the present invention.

FIGS. 11A and 11B (collectively FIG. 11) are illustrations of an electromagnetic wave of light propagating along an optical waveguide in accordance with certain exemplary embodiments of the present invention.

Figure 8A:
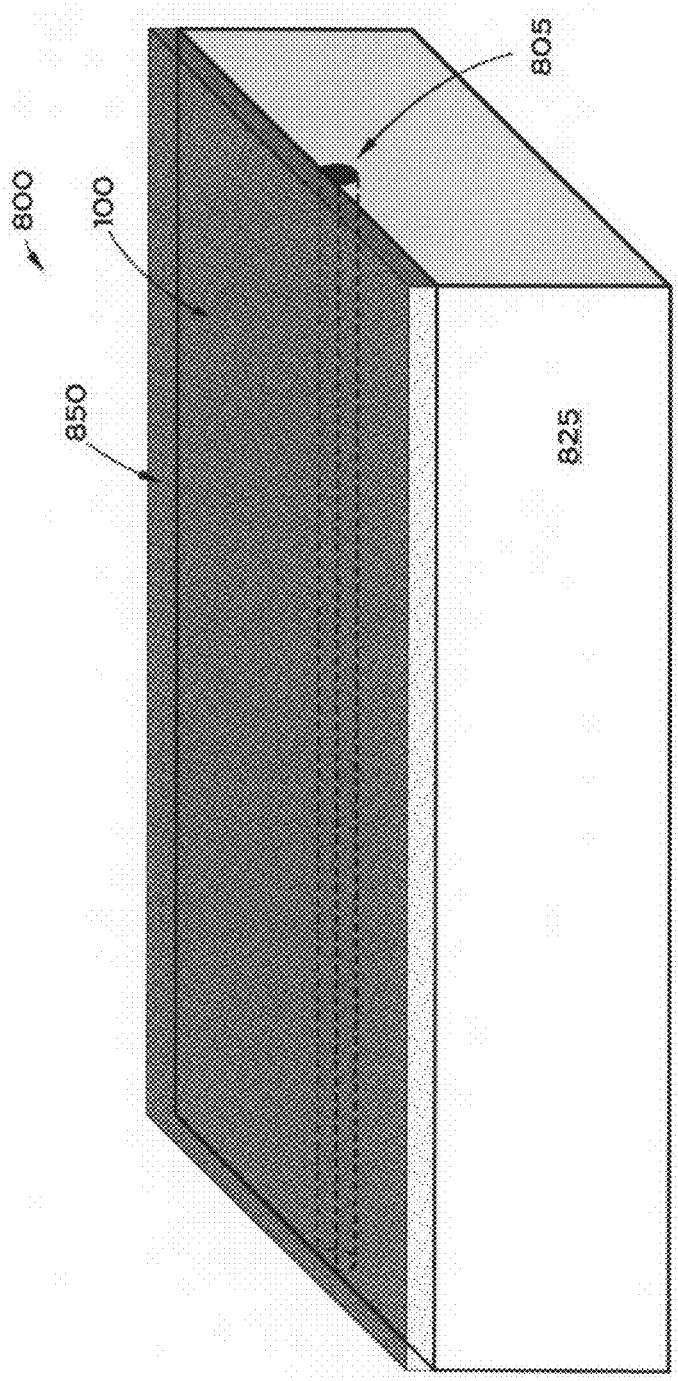
FIGS. 8A, 8B, and 8C (collectively FIG. 8) are illustrations of a substrate comprising an integrated optical waveguide coated with an optical material that comprises polymeric material and gas-filled bubbles in accordance with certain exemplary embodiments of the present invention.

Many aspects of the present invention can be better understood with reference to the above figures. The elements and features shown in the figures are not necessarily to scale, emphasis instead being placed upon clearly illustrating principles of exemplary embodiments of the present invention. Moreover, certain dimensions may be exaggerated to help visually convey such principles. In the figures, reference numerals designate like or corresponding, but not necessarily identical, elements throughout the several views.

DETAILED DESCRIPTION OF EXEMPLARY EMBODIMENTS

Certain exemplary embodiments of the present invention support decreasing refractive index of an optical material via creating pockets of gas in the material that are substantially smaller than the wavelength of the light that the material is intended to handle. The resulting material can be utilized, to mention a few representative examples, to create internally reflective surfaces, prisms, optical fibers, planar light guide circuits, high numerical aperture devices, Bragg reflectors, thin-film interference filters, anti-reflective coatings, encapsulants, optical elements, lenses, and numerous other systems that would benefit from a low index of refraction.

The present invention can be embodied in many different forms and should not be construed as limited to the embodiments set forth herein; rather, these embodiments are provided so that this disclosure will be thorough and complete, and will fully convey the scope of the invention to those having ordinary skill in the art. Furthermore, all "examples," "embodiments," and "exemplary embodiments" given herein are intended to be non-limiting, and among others supported by representations of the present invention.

This document includes sentences, paragraphs, and passages (some of which might be viewed as lists) disclosing alternative components, elements, features, functionalities, usages, operations, steps, etc. for various embodiments of the present invention. Unless clearly stated otherwise, all such lists, sentences, paragraphs, passages, and other disclosures are not exhaustive, are not limiting, are provided in the context of describing representative examples and variations, and are among others supported by various embodiments of the present invention. Moreover, the items in such lists and other disclosed alternatives are not necessarily mutually exclusive and thus may be overlapping. A single embodiment of the present invention can include multiple items from a disclosed set of alternatives, whether the set is disclosed herein using the conjunction "or," in the form of a Markush group, as a list, or otherwise enumerated. Those of ordinary skill in the art having benefit of this disclosure will appreciate that the present invention is not constrained by any such lists, examples, or alternatives. Moreover, the inclusion of lists, examples, embodiments, and the like will help educate and guide those of ordinary skill in the art to practice many more implementations and instances of the present invention without undue experimentation, all of which are intended to be within the scope of the claims.

This disclosure includes figures and discussion in which features and elements of certain embodiments may be organized into functional blocks, subsystems, modules, or the like. Further, certain processes and methods may be organized into steps. Such organization is intended to enhance readership and to teach the reader about working principles of the present invention and about making and using an abundance of embodiments of the present invention. The organization is not intended to force any rigid divisions or partitions that would limit the present invention. In practice, the flexibility of the present invention supports dispersing, rearranging, or grouping functionalities, elements, and features in many different ways. The inclusion of an element or function in one block, module, or subsystem verses another can be substantially arbitrary in many instances, with the divisions being soft and readily redrawn using this rich disclosure supported by ordinary skill. Accordingly, functional blocks, modules, subsystems, and the like can be combined, divided, repartitioned, redrawn, moved, reorganized, rearranged, or otherwise altered without deviating from the scope and spirit of the present invention. This is not to say that certain disclosed organizations and combinations are not novel or are obvious. The way certain features of the present invention relate to and interact with one another is new. Accordingly, combinations, arrangements, or organizations disclosed herein can represent innovative subject matter.

Figure 12:
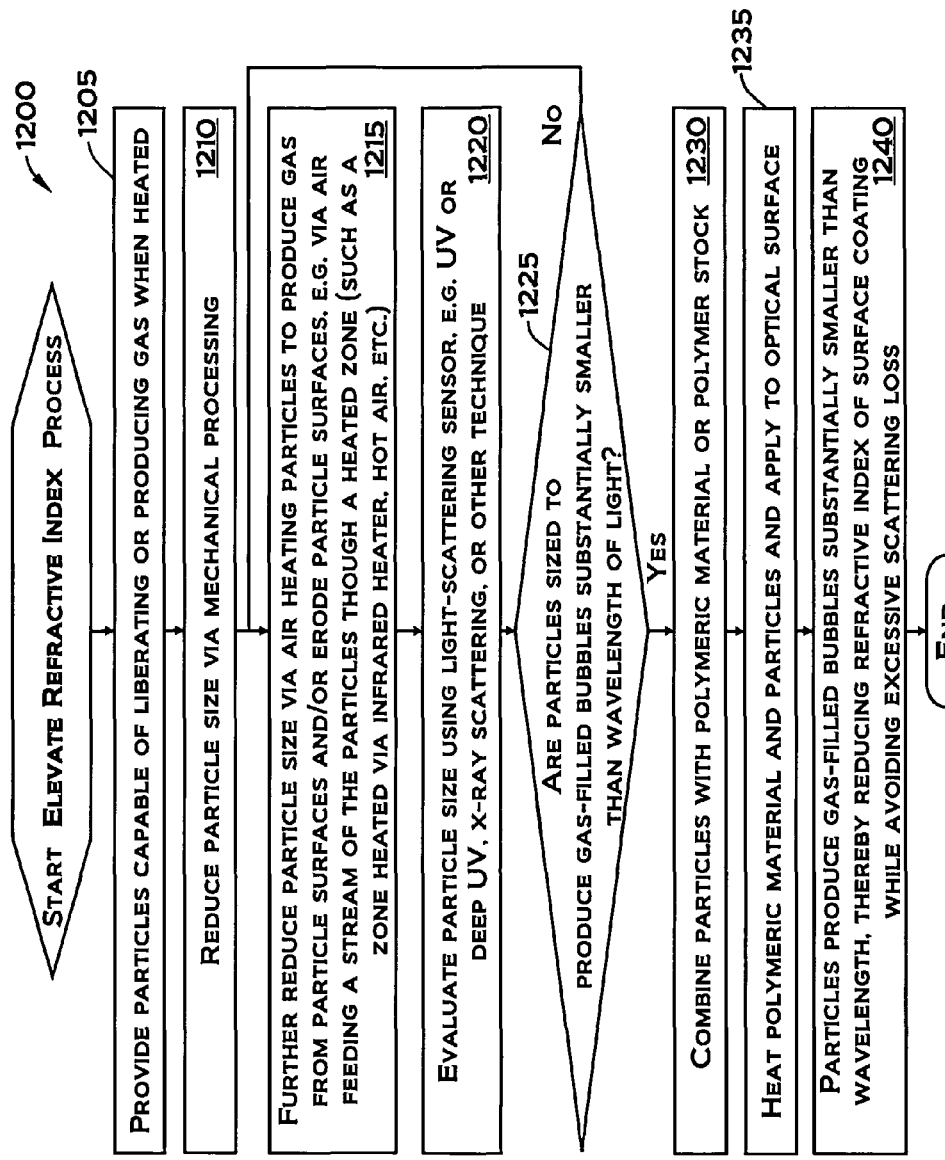
FIG. 12 is a flowchart of a process for elevating refractive index of a material in accordance with certain exemplary embodiments of the present invention.
Figure 13:
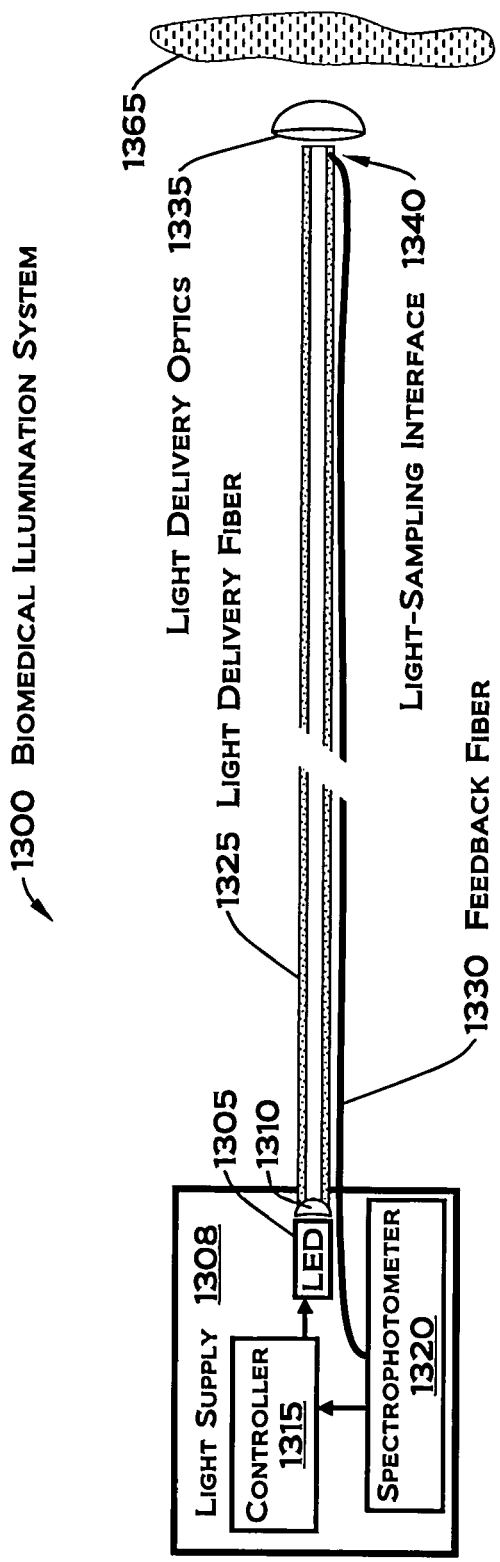
FIG. 13 is a functional block diagram of a light delivery system in accordance with certain exemplary embodiments of the present invention.
Figure 14:
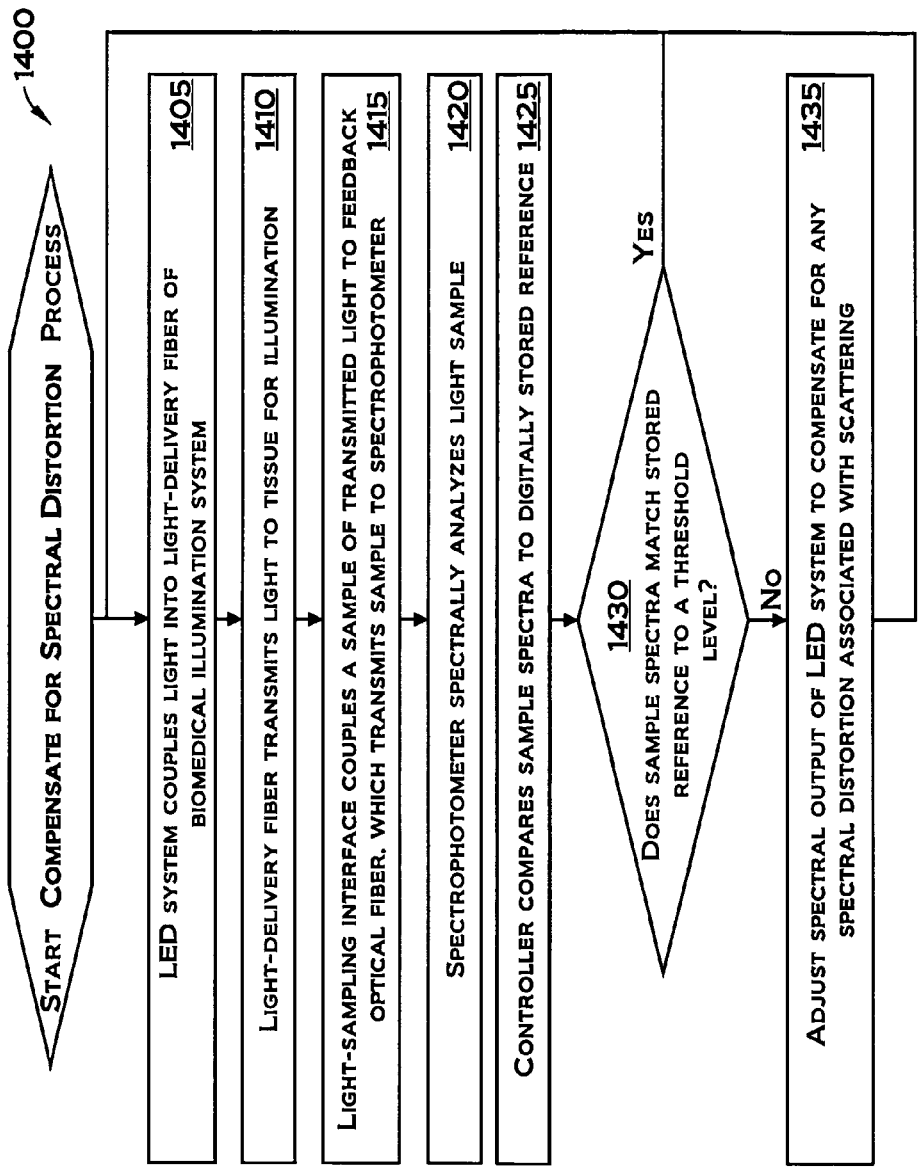
FIG. 14 is a flowchart of a process for compensating for spectral distortion associated with light scattering in accordance with certain exemplary embodiments of the present invention.
Figure 15:
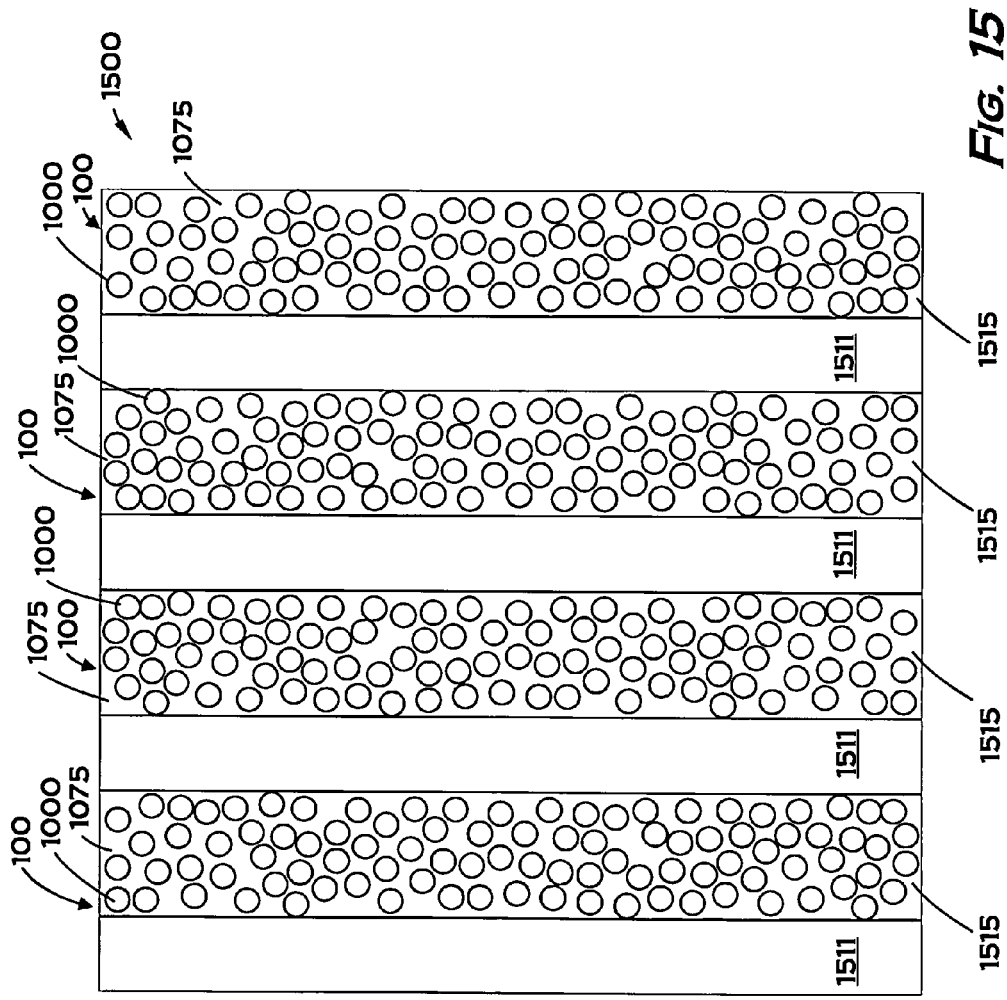
FIG. 15 is an illustration of an optical system comprising layers of a first optical material interleaved between layers of a second optical material that comprises polymeric material and gas-filled bubbles in accordance with certain exemplary embodiments of the present invention.

The present invention will be discussed more fully hereinafter with reference to FIGS. 1-15, which provide additional information regarding representative or illustrative embodiments of the present invention. FIGS. 1-7 describe fiber optic systems that comprise internally reflective surfaces formed with an optical material having an enhanced refractive index. FIGS. 8-11 describe light propagation and waveguides that include an optical material having an enhanced refractive index. FIG. 12 describes a process for enhancing refractive index of an optical material. FIGS. 13 and 14 describe a light delivery system that includes an enhanced refractive index material. FIG. 15 describes a periodic structure comprising layers of an optical material having an enhanced refractive index.

Turning now to FIG. 1, this figure illustrates an exemplary fiber optic system 2700 comprising an internally reflective surface 2720 formed at an interface between silica and an exemplary optical material 100 comprising polymeric material and gas-filled bubbles according to certain embodiments of the present invention. The fiber optic system 2700 can function as a fiber optic probe or catheter for delivering and collecting light in connection with performing spectral analysis, optical sensing, or light-based characterization as discussed in U.S. Pat. No. 5,953,477 to Wach et al. entitled "Method and Apparatus for Improved Fiber Optic Light Management," the entire contents of which are hereby incorporated herein by reference and as discussed in U.S. Pat. No. 6,580,935 to Wach et al. entitled "Method and System for Stabilizing Reflected Light," the entire contents of which are hereby incorporated herein by reference. In certain exemplary embodiments, a distal end of a cardiac catheter comprises the fiber optic system 2700 for analyzing atherosclerotic plaque, lesions, or other material or tissue in a vascular lumen. Accordingly, the fiber optic system 2700 can be sized for lengthwise insertion in the human vasculature.

The fiber optic system 2700 that FIG. 1 illustrates comprises a central optical fiber 2710 circumferentially surrounded by a ring of optical fibers 2715. To fabricate the fiber optic assembly 2700, the ring optical fibers 2175 and central optical fiber 2710 can be bonded together and ground and polished as a unit, analogous to sharpening a pencil tip, to form the internally reflective surface 2720 on the ring optical fibers 2715. The internally reflective surface 2720 is coated with the optical material 100 having a low refractive index supporting internal reflection. As will be discussed in further detail below, in an exemplary embodiment, the optical material 100 comprises a polymer having desirable optical properties and a refractive index that is enhanced via additional of extremely small pockets, voids, inclusions, or bubbles of gas for lowering refractive index.

The unit of ring optical fibers 2715 and central optical fiber 2710 is encased in a sleeve 2730, which can be metallic, plastic, glass, composite, ceramic, or some other appropriate material. Any gaps between the coating of the optical material 100 and the sleeve 2730 can be filled with another material 250 that may be opaque or light absorbing. Alternatively, more of the optical material 100 can be incorporated to fill this gap. Accordingly, the optical material 100 can be applied over the internally reflective surface 2720 as a thin coating, a deposited thin or thick film, a thick conformal coating, a dip, or as an encapsulant, and the surface 2720 can be embedded or buried in the optical material 100.

In operation, the internally reflective surface 2720 directs or steers the pattern of light delivery or light collection of the ring optical fibers 2715 in front of or towards the central optical fiber 2710. By utilizing a coating with a very low refractive index, the internally reflective surface 2710 supports total internal reflection at a greater angle than if the coating had a somewhat higher refractive index. Accordingly, the enhanced refractive index of the optical material 100 can provide light management and aggressive beam steering.

In certain exemplary embodiments, the central optical fiber 2710 of the fiber optic system 2700 is replaced with a channel, such as a silica capillary tube or other suitable tube. Accordingly, the element denoted "2710" in FIG. 1 can comprise an optical fiber in certain embodiments and a tube in certain other embodiments and will be discussed below with reference to the latter embodiments as "the tube 2710."

In certain exemplary embodiments, the fiber optic system 2700 comprises another embodiment of a channel. For example, the channel can comprise one or more interstitial spaces that extend lengthwise within a group of optical fibers, such as in openings between the central optical fiber 2710 and the ring optical fibers 2715.

In certain exemplary embodiments, the tube 2710 can comprise (or substantially consist of) glass, silica, silicate, or quartz. The tube 2710 can have an outer diameter that is substantially consistent with the diameters of the ring optical fibers 2715. Appropriate capillary tubing for the tube 2710 is available from Polymicro Technologies of Phoenix, Ariz.

The tube 2710 can deliver a fluid or liquid (including a mixture or suspension) that facilitates analysis or assay of a material, sample, organ, or tissue disposed adjacent the distal, illustrated end of the fiber optic system 2700. So equipped, the fiber optic system 2700 can be utilized for in vivo analysis, such as via insertion into a human, mammal, vertebrate, organism, test subject, patient, or living tissue; deployed for in situ analysis of materials or processes; or utilized on ex vivo tissues or extracted specimens, for example.

In accordance with various exemplary embodiments, a fluid emitted from the tube 2710 can comprise a dye; a fluorescent material; one or more tags; an indicator; a sensing compound; a material that, when appropriately illuminated, fluoresces in the presence of a physical condition, disease state, tissue condition, chemical condition, or other parameter or stimulus of interest; a chemical probe; a fluorescent probe; a fluorescent or other probe for detecting and/or quantitatively analyzing one or more reactive oxygen species, such as superoxide and/or hydroxyl radicals; a reduced dye probe for the detection of radical oxygen species, a stain; a reference material; a contrast agent; a signal enhancer; quantum dots; nanoparticles; a material that induces, undergoes, or facilitates surface enhanced Raman scattering ("SERS"); an agent that induces, facilitates, causes, or stimulates an optical response; a material that undergoes or produces a color or spectroscopic change or optical response in the presence of an analyte of interest; a reactant; a reagent; a fluid that is useful for diagnostics; a diagnostic material; a reaction initiator; a catalyst; or some other useful agent or combination thereof, to mention a few representative examples.

In certain exemplary embodiments, the tube 2710 delivers a pharmaceutical agent, drug, or other therapeutic material or agent, to tissue in connection with evaluating interaction between the agent and tissue. Thus, the fiber optic system 2700 can evaluate drug-tissue interactions. For example, a pharmaceutical manufacturer or developer may be interested in investigating how an agent responds to tissue and/or how tissue responds to an agent. The fiber optic system 2700 can be inserted into the tissue and/or disposed against the tissue. So oriented, the fiber optic system 2700 can emit the agent onto or into the tissue through the tube 2710. The fiber optic system 2700 can then deliver light to and collect light from the tissue (and/or the emitted or emitting agent) to conduct light-based characterization of the delivered pharmaceutical agent and/or the tissue.

In certain exemplary embodiments, a first one of the ring optical fibers 2715 delivers excitation light while the other ring optical fibers 2715 collect response light. Next, a second ring optical fiber 2715 delivers excitation light while other ring optical fibers 2715 collect response light. In this manner, each ring optical fiber 2715 can take a turn emitting light, with the other ring optical fibers 2715 collecting light. Such sequencing provides spatial analysis of vascular lumens, interior surfaces of vascular lumens, tumors, and various tissue structures.

In certain other exemplary embodiments, the ring optical fibers 2715 simultaneously emit and receive light, with each ring optical fiber 2715 optically characterizing a distinct spatial area or volume. (All ring optical fibers 2715 can emit and receive light at the same time, or take turns simultaneously emitting and receiving light.) For fluorescent analysis, the proximal end of the fiber optic system 2700 can be coupled to a light source, for example a laser, and a detector, for example a charge coupled device with an associated spectrophotometer or spectrograph. One or more optical filters, which may be located distally or proximally, can separate the outgoing light from the incoming light.

In certain exemplary embodiments, the tube 2710 can have sidewalls that are substantially transparent to facilitate transmitting light through the sidewalls at the distal end. So equipped, the fiber optic system 2700 can analyze and image right at the distal aperture of the tube 2710.

Beyond developmental applications, this technique can be utilized in therapy and/or clinical applications so that effectiveness of a treatment on an individual patient can be assessed, thereby supporting personalized medicine. For example, test quantities of multiple agents can be injected into a tumor (either at the same time or sequentially) through one or more instances of the fiber optic system 2700. The fiber optic system(s) 2700 can then be utilized to evaluate the tumor's responses to the individual agents, for example based on oxidation, inflammation, superoxide, reactive oxygen species, hydroxyl radicals, or metabolites. A therapeutic dose of the agent that generated the greatest beneficial response can then be delivered for effect.

In this manner, responses of tumors or lesions to various therapies, treatments, compounds, drugs, toxins, bacteria, viruses, yeasts, pathogens, parasites, cells, stem cells, progenitor cells, cells that can differentiate, therapeutic cells, therapeutic agents, and/or pharmaceutical agents can be assessed and/or investigated. The technique is further applicable to numerous organs, tissues, and disease states, including cardiovascular disease, atherosclerosis, brain tissues, adipose tissue, pancreases, kidneys, skin, colon, stomach, intestines, necrotic myocardial tissue, ischemic myocardial tissue, digestive tract, thyroid, spleen, liver, auditory system, ocular organs, eyes, ears, esophagus, blood, bladder, prostate, uterine tissue, reproductive systems, ovaries, circulatory system, lymphatic system, throat, lungs, bone marrow, cartilage, muscular tissue, myocardial tissues, and nerves, and various diseases and treatments thereof, to name a few representative examples.

In certain exemplary embodiments, the tube 2710 delivers stem cells to infracted myocardial tissue, an injured spinal cord, or infracted brain tissue of a living laboratory animal in which the fiber optic system 2700 has been implanted. The fiber optic system 2700 then monitors response of the animal's myocardial tissue, spinal cord, or brain to the stem cells and can further monitor response of the stem cells to delivery in such living tissue. With the fiber optic system 2700 so implanted, an investigator or medical practitioner can monitor responses and changes over hours, days, weeks, or months, for example. The investigator or practitioner gains a real-time window into changes that might otherwise be too subtle or fleeting to detect utilizing convention post-mortem analysis. In this manner, the investigator can develop effective therapies and protocols and can observe responses that would otherwise be hidden. For example, the fiber optic system 2700 can conduct a Raman analysis to determine metabolites and/or metabolic responses at a precise treatment area.

In certain exemplary embodiments, the tube 2710 delivers a substance that indicates oxidation, presence and/or concentration of a reactive oxygen species, a radical oxygen species, superoxide, and/or hydroxyl radicals occurring in tissue and/or inflammation, such as one or more of the substances, agents, probes, dyes, or other materials disclosed in the patent application published as International Publication Number WO 2009/121,055 entitled "*Reduced Dye Probes for the Detection of Radical Oxygen Species*" and naming Niren Murthy, Robert W. Taylor, Kousik Kundu, and Sarah F. Knight as inventors, the entire contents of which are hereby incorporated herein by reference. For example, the illustrated end of the fiber optic system 2700 can be disposed adjacent tissue of interest, such as in a diseased vascular lumen, artery, or blood vessel of a patient or test subject or in or adjacent a tumor of a patient or test subject. Disposed lengthwise in a vascular lumen adjacent an atherosclerotic lesion or plaque, the fiber optic system 2700 can evaluate propensity to rupture based on fluorescence response of the delivered substance to excitation light. A plaque having a low vulnerability to rupture, and thus representing a relatively low risk, typically produces relatively low fluorescence as its inflammation and oxidation is low. Conversely, "vulnerable plaque" typically produces heightened fluorescence from the substance.

Turning now to FIG. 2, this figure illustrates an exemplary fiber optic system 200 comprising a tapered optical fiber, wherein the taper 220 is coated with an exemplary optical material 100 comprising polymeric material and gas-filled bubbles according to certain embodiments of the present invention. As discussed in U.S. Pat. No. 5,953,477, the included angle 260 of the taper 220 controls the angle 212 of the emission/collection pattern 210, for example between 17 degrees and 78 degrees as illustrated.

The taper 220 is at the tip of an untapered section of optical fiber 230 and can be formed via grinding and polishing or other technique known in the art. The surface 275 of the taper 220 is coated with the optical material 100 to form an internally reflective interface for angularly manipulating light entering or leaving the fiber optic system 200. Accordingly, the taper 220 and the accompanying optical material 100, which has an enhanced refractive index, control numerical aperture of the fiber optic system 200 and/or the system's pattern of light acceptance and delivery. The untapered section 230 of optical fiber, which may be single mode or multimode, includes a core 232 and a cladding 231, with the core 232 having a higher refractive index than the cladding 231 to facilitate total internal reflection. For example, the core 232 and the cladding 231 can each comprise silica or silicon dioxide, with an additive such as germanium in the core 232 elevating the refractive index of the core 232 above the cladding 231.

An optional tube 240 circumferentially surrounds the taper 220 and a portion of the untapered section 230 and can comprise metal, ceramic material, pliable polymer, rigid material, heat shrink, a composite system, glass, or some other appropriate material or sleeving. The tube 240 provides a level of mechanical protection that may benefit certain applications while being unnecessary in others. A material 250 can be applied in any open space between the tube 240 and the taper surface 275 that may be void of the optical material 100, thereby filling such an open space. The material 250 can be an epoxy that may be opaque or transparent or some other appropriate substance. Alternatively, in certain embodiments, the optical material 100 fills the volume between the tube 240 and the taper surface 275 (so few if any voids exist to be filled).

The low refractive index of the optical material 100 supports a wide range of included angles 260 for the taper 220 operating in a total internal reflection regime. Lowering the refractive index generally facilitates increasing the included angle 260 that can support total internal reflection of light entering or exiting the fiber optic system 200. With the angle 260 so increased, the angle 212 can increase, and the fiber optic system 200 can manipulate light aggressively. For example, the emission/collection pattern 210 might be limited to 25 degrees with the surface 275 of the taper 220 coated with a conventional optical polymer. However, the emission/collection pattern 210 might be extended to 78 degrees via lowering the optical polymer's refractive index (as discussed below) and utilizing a more aggressive included angle 260. That is, the enhanced refractive index of the optical material 100 facilitates increasing the angle 260 while avoiding light unwontedly spilling out of the sides of the taper 220. (Those skilled in the art having benefit of this disclosure will appreciate that actual angular values may depend at least upon the optical characteristics and fill of the untapered section 230 and the refractive index of the ambient medium.)

Turning now to FIG. 3, this figure illustrates an exemplary optical fiber 300 having a beam manipulating feature that includes an exemplary coating of optical material 100 exhibiting a low refractive index and comprising polymeric material and gas-filled bubbles according to certain embodiments of the present invention.

More specifically, the optical fiber 300 comprises a substantially flat surface 325 that can be formed near the end of the optical fiber 300 via grinding and polishing or other appropriate material removal or forming technique. In an exemplary embodiment, the flat surface 325 is coated with an optical material 100 having a refractive index that is lowered via addition of extremely small features filled with a gas such as air, nitrogen, helium, hydrogen, etc. The optical material 100 has a substantially lower refractive index than the base optical fiber 300 itself, including any core or cladding thereof. Accordingly, light propagating in the optical fiber 300 towards the illustrated end is internally reflected and kicked out by the interface between the fiber's core material and the optical material 100 that is applied to the surface 325. Further, light entering the optical fiber 300 that is incident upon the surface 325 and that would otherwise not be carried by the optical fiber 300 is redirected for conduction by the optical fiber 300.

The low refractive index of the optical material 100 facilitates orienting the surface 325 at a steep angle relative to the longitudinal axis of the optical fiber 300 while supporting total internal reflection. If a different optical material having a refractive index higher than the optical material 100 but still lower than the refractive index of the core and cladding of the optical fiber 300 was utilized, then the orientation of the surface 325 would typically be limited to less aggressive angles in order to support total internal reflection of waveguided light. Thus, the enhanced refractive index of the optical material 100 supports greater flexibility in the orientation of the surface 325 and a wider range of light management options. While suited for many applications, in certain embodiment, the optical fiber 300 is an element of a medical device, such as a catheter that may navigate a vascular lumen of a patient or a test subject.

Turning now to FIG. 4, this figure illustrates an exemplary optical fiber 400 having a beam manipulating feature that includes an exemplary coating of optical material 100 exhibiting a low refractive index and comprising polymeric material and gas-filled bubbles according to certain embodiments of the present invention. The optical fiber 400 comprises a three-dimensional surface 425 formed near its tip for steering light entering and/or exiting the optical fiber 400. The surface 425 can be coated with the optical material 100 having a refractive index that is enhanced so as to be lowered. With such an enhanced refractive index, the surface 425 can be formed with a greater range of contours and orientations while supporting total internal reflection. The optical material 100 supports configuring the optical fiber 400 for aggressive light manipulation, and the pattern of light receptivity or emission can diverge steeply from the longitudinal axis of the optical fiber 400. In certain embodiments, a medical catheter that diagnoses disease can comprise the optical fiber 400.

Turning now to FIG. 5, this figure illustrates an exemplary optical fiber 500 having a beam manipulating feature that includes an exemplary coating of optical material 100 exhibiting a low refractive index and comprising polymeric material and gas-filled bubbles according to certain embodiments of the present invention. The optical fiber 500 comprises a contoured, convex surface 525 coated with optical material 100 comprising features for providing a lowered refractive index and providing an internally reflective interface. As shown in FIG. 5C, the contoured, convex surface 525 reflects light rays 510 that may be either entering or exiting the optical fiber 500. In certain embodiments, a cardiac catheter that is sized for lengthwise insertion in a vascular lumen of a patient can comprise the optical fiber 500 for managing light entering or exiting the catheter, for example.

Turning now to FIG. 6, this figure illustrates an exemplary fiber optic system 6000 comprising internally reflective surfaces 6850, 6855 formed at interfaces between silica and an optical material 100 comprising polymeric material and gas-filled bubbles according to certain embodiments of the present invention. The system 6000 includes multiple optical fibers 6875 tipped with prisms 6850 coated with the optical material 100. The resulting internally reflective surfaces 6855 direct incoming light rays 6100 to an appropriate angle for transmission over the optical fibers 6875. Optical filters 6860 are disposed at the ends of the optical fibers 6875 between the fibers 6875 and the prisms 6850, while the optical filter 6855 is located between the optical fiber 6875 and a short segment of optical fiber 6840. In certain exemplary embodiments, the optical filters 6860 can comprise the optical material 100, for example as illustrated in FIG. 15 and discussed below. In certain exemplary embodiments, in addition to the prisms 6850, the optical fibers 6875 can be coated or clad with the optical material 100. Thus, the optical material 100 can provide either a primary cladding or a secondary cladding.

In certain exemplary embodiments, the fiber optic system 6000 comprises one or more channels for delivering a material that facilitates light-based characterization of an adjacent analyte or a sample, which may be either in situ or extracted. As discussed above with reference to FIG. 1, in certain embodiments, such a material can have a fluorescence response that changes according to composition and/or disease state of the analyte or sample. The term "analyte," as used herein, generally refers to a substance or biological or chemical constituent that is the subject of analysis. (In the event that any documents incorporated by reference might be interpreted as supporting a different usage for the term "analyte," the usage in the preceding sentence should apply to the claims of the present application as well as the claims of any patent issuing on the present patent application and the claims of any patent(s) claiming priority to the present application.) In certain exemplary embodiments, the delivered material can comprise a reagent. The term "reagent," as used herein, generally refers to a substance having chemical and/or biological activity for detecting, measuring, or otherwise analyzing one or more other substances. (In the event that any documents incorporated by reference might be interpreted as supporting a different usage for the term "reagent," the usage in the preceding sentence should apply to the claims of the present application as well as the claims of any patent issuing on the present patent application and the claims of any patent(s) claiming priority to the present application.) The light-based characterization can be a quantitative assay, for example. In certain exemplary embodiments, interstitial space between or among the optical fibers 6875 provides the channel. In certain exemplary embodiments, one of the optical fibers 6875 is replaced with a tube that delivers the material, for example as a fluid or a liquid.

Turning now to FIG. 7, this figure illustrates an exemplary fiber optic system 6500 comprising an internally reflective surface 6545 formed at an interface between silica and an optical material 100 comprising polymeric material and gas-filled bubbles according to certain embodiments of the present invention. The system 6500 includes multiple optical fibers 6510, 6580 for emitting light 6501 and receiving light 6540, 6590. The optical fibers 6580 are collectively contoured at their ends for manipulating incoming light 6540 to facilitate waveguided propagation. The optical fibers 6580 are coated with the optical material 100 at the surface 6545, thereby enhancing numerical aperture and/or steering light. In certain exemplary embodiments, the surface 6595 of the optical fiber 6510 is coated with the optical material 100 to provide enhanced numerical aperture for light delivery.

In certain exemplary embodiments, the fiber optic system 6500 comprises one or more channels for delivering an indicator or a reagent to facilitate in vivo analysis of tissue or other materials disposed in an organism. In certain exemplary embodiments, the fiber optic system 6500 comprises multiple channels, each delivering a different reagent, either simultaneously or sequentially. One reagent may be used for a reference, while another reagent may be used as discussed above with reference to FIGS. 1 and 6. In certain exemplary embodiments, the two reagents interact with one another when combined at the tip of the fiber optic system 6500, for example to facilitate an in vivo assay. In certain exemplary embodiments, two materials emitted from the fiber optic system 6500 undergo a chemical reaction with one another after emission, and the reaction product facilitates an assay or analysis.

In certain exemplary embodiments, the illustrated, distal end of the fiber optic system 6500 is disposed in a vascular lumen substantially coaxially with the lumen. In this configuration, the fiber optic system 6500 can function like a fisheye lens, to image the interior surface of the vascular lumen. Thus, the fiber optic system 6500 can conduct analyses of tissue disposed laterally with respect to the fiber optic system 6500. The image can provide chemical and/or structural information about plaque disposed on the interior surface of the vascular lumen, for example to assess vulnerability to rupture.

Turning now to FIG. 8, this figure illustrates an exemplary substrate 825 comprising an integrated optical waveguide 800 coated with an exemplary optical material 100 that comprises polymeric material and gas-filled bubbles according to certain embodiments of the present invention. The optical material 100 effectively provides a cladding 850 for the optical waveguide core 805 of the optical waveguide 800. In certain exemplary embodiments, a PLC can comprise the optical waveguide 800.

The term "optical waveguide," as used herein, generally refers to a device or structure that directs, controls, or steers light to flow along a path, course, route, or channel and confines, limits, or binds the light so the light generally says on or in the path, course, route, or channel. An optical waveguide can comprise one or more structures that guide and/or generally confine light during transmission. For example, such an optical waveguide can comprise an elongate or elongated section of optical material that has high refractive index relative to an adjacent material, such as a cladding. In this configuration, the cladding helps keep the light on course. Another type of optical waveguide can comprise a material with a pattern of structures, such as holes, that help transmitting light maintain a prescribed course of travel without unwanted or excessive divergence or loss. An optical waveguide can be either multimode or single mode (also known as "mono-mode").

Figure 8B:
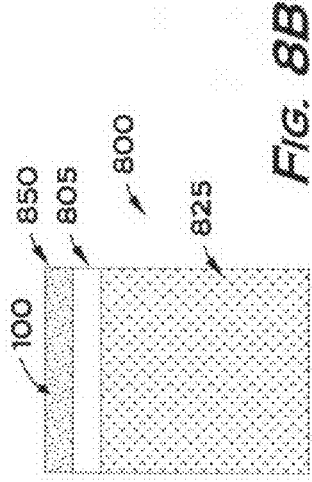

Referring to FIGS. 8A and 8B, in an exemplary embodiment, the substrate 825 comprises glass, such as silicate glass, and the optical waveguide core 805 is formed via ion exchange. Accordingly, the optical waveguide core 805 can comprise a region extending along, alongside, or beside a surface of the substrate 825 in which exchanged ions have provided an elevated refractive index. In such an embodiment, the substrate 825 provides cladding for one side of the optical waveguide core 805. The optical material 100 provides cladding 850 for the other side of the optical waveguide core 805. The substrate 825 and the optical material 100 thus fully clad the optical waveguide core 805 for the optical waveguide 800, which may be multimode or single mode.

Various waveguide fabrication processes known in the art other than ion exchange can be utilized to fabricate embodiments of the optical waveguide 800. In certain exemplary embodiments, a silica-on-silicon PLC, a photonic integrated circuit ("PIC"), a ribbed waveguide, a silicon photonic system, an on-chip optical communication network or line, a photonic chip, a chip, a bus or link for a multicore computer processor, an optical bus, a backplane communication line, an integrated optical device, or some other optical system can comprise the optical waveguide 800, for example. Accordingly, a wide variety of integrated optical systems and devices can comprise the optical material 100 as part of an optical waveguide, to increase numerical aperture, to form a totally internally reflective surface, to manage light, or for another appropriate application benefiting from the optical material's enhanced optical characteristics.

In various exemplary embodiments, the optical material 100 can be applied, following ion exchange, via spin coating, dip application, extrusive overcoat, extrusion, melting, conformal coating, or another appropriate process, for example.

Figure 8C:
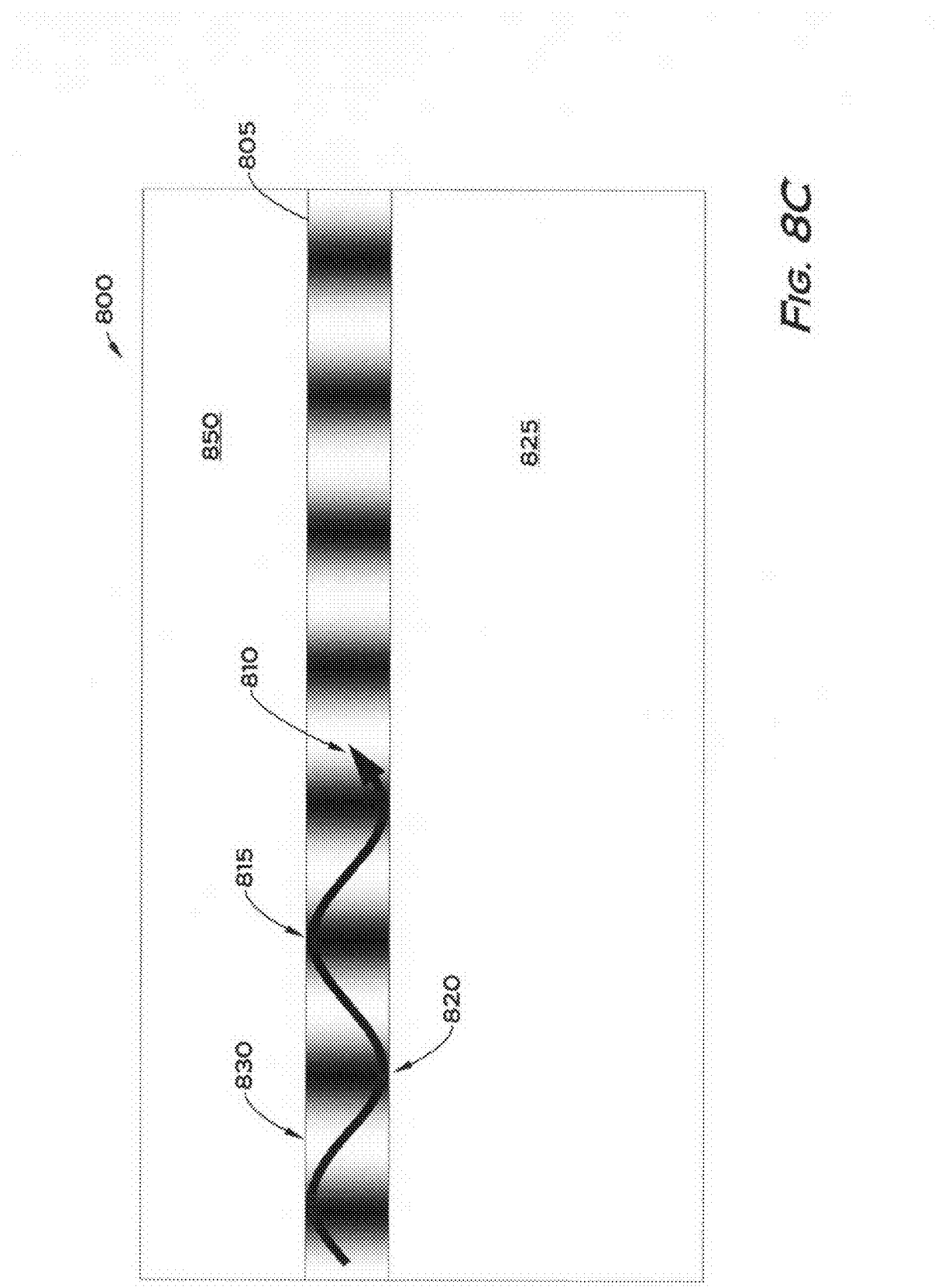

Referring now to FIG. 8C, this figure illustrates an exemplary electromagnetic wave of light 810 propagating along the optical waveguide core 805 of the optical waveguide 800. The electromagnetic wave of light 810 comprises crests 815 and troughs 820 in which electrical field strength reaches maximum positive and maximum negative values respectively. The electromagnetic wave of light 810 further comprises zero-crossing regions 830 in which electrical field strength is transitioning between positive and negative values and/or is xsubstantially reduced. Accordingly, FIG. 8C illustrates field intensity along the optical waveguide 800 for exemplary coherent, monochromatic light. In practice, the optical waveguide 800 can carry numerous colors or wavelengths of light simultaneously and such light can be either coherent or incoherent, polarized or non-polarized, and/or multimode or single mode.

Turning now to FIG. 9, this figure illustrates an exemplary plot 900 of an exemplary electromagnetic wave of light 810 according to certain embodiments of the present invention. In an exemplary embodiment, the electromagnetic wave of light 810 illustrated in FIG. 9 can be the electromagnetic wave of light 810 illustrated in FIG. 8C and discussed above. The illustrated electromagnetic wave of light 810 can further exemplify light propagating in an unguided or free-space medium, for example traveling through air for incidence on a prism, lens, optic, or other optical element coated with the optical material 100.

As illustrated in FIG. 9 and without being bound by theory, the exemplary electromagnetic wave of light 810 comprises an electric field component 915 and a magnetic field component 910 oscillating perpendicular to each other, perpendicular to the longitudinal axis of the optical waveguide 805 (the direction of propagation), and in phase with one another. The plot 900 illustrates the wavelength 975 of the electromagnetic wave of light 810, in this case depicted between two adjacent crests 815.

In certain exemplary embodiments, the wavelength 975 (often conventionally represented by the Greek letter "lambda") is in a visible range of the electromagnetic spectrum. In certain exemplary embodiments, the optical waveguide 805 carries visible light, for example having wavelength 975 in a range of about 380 nanometers ("nm") to about 750 nm.

In certain exemplary embodiments, the wavelength 975 can be consistent with light that comprises ultraviolet ("UV"), vacuum UV, deep UV, violet (typically 380-450 nm or 668-789 THz), indigo (typically 420-450 nm or 668-714 THz), blue (typically 450-495 nm or 606-668 THz), green (typically 495-570 nm or 526-606 THz), yellow (typically 570-590 nm or 508-526 THz), orange (typically 590-620 nm or 484-508 THz), red (typically 620-750 nm or 400-484 THz), infrared, near infrared (750-2,500 nm or 120-400 THz), mid-infrared (2,500-10,000 nm or 30-120 THz) or some other appropriate color, wavelength, or frequency. The wavelength ranges and associated terms provided in this paragraph are intended to conform generally with accepted industry usage, as would be appreciated by one of ordinary skill in the art.

In certain exemplary embodiments, the electromagnetic wave of light 810 could be exactly one photon. In certain exemplary embodiments, the electromagnetic wave of light 810 represents a plurality or stream of photons produced by a single source or emitted through a common aperture, and the photons may or may not be in phase with respect to one another.

Figure 10:
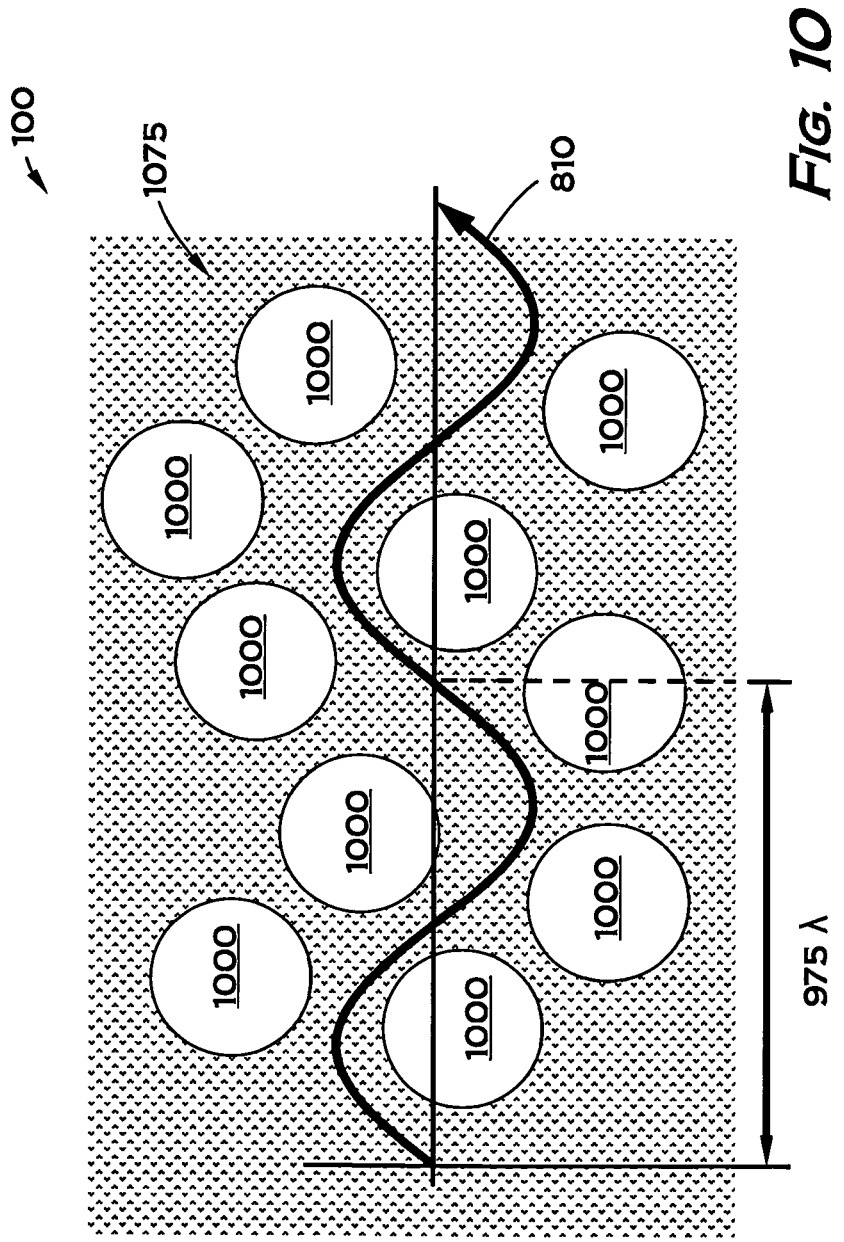
FIG. 10 is an illustration of an electromagnetic wave of light propagating through an optical material that comprises polymeric material and gas-filled bubbles in accordance with certain exemplary embodiments of the present invention.

Turning now to FIG. 10, this figure illustrates an exemplary electromagnetic wave of light 810 propagating through an exemplary optical material 100 that comprises polymeric material 1075 and gas-filled bubbles 1000 according to certain embodiments of the present invention. The optical material 100 illustrated in FIG. 10 can be an exemplary embodiment of the optical material 100 illustrated in previous figures and discussed above.

The exemplary gas-filled bubbles 1000 in the illustrated optical material 100 are dimensioned smaller than a wavelength 975 of the electromagnetic wave of light 810 and avoid excessive scattering. In certain exemplary embodiments, every dimension of the gas-filled bubbles 1000 is smaller than such a wavelength 975. In certain exemplary embodiments, the gas-filled bubbles 1000 may have an elongated or expanded dimension, and that dimension can be smaller than the wavelength 975 of the electromagnetic wave of light 810.

Speaking intuitively and perhaps relaxing scientific rigor, the electromagnetic wave of light 810 can flow around the gas-filled bubbles 1000, conceptually like FIG. 10 illustrates. Without being bound by theory, the phenomenon is believed to be analogous to the situation whereby long-wavelength radio waves tend to "bend" around buildings and objects in their path more so than short-wavelength radio waves.

Turning now to FIG. 11, this figure illustrates an exemplary electromagnetic wave of light 810 propagating along an exemplary optical waveguide 800 according to certain embodiments of the present invention. The optical waveguide 800 illustrated in FIG. 11 can be an embodiment of the optical waveguide 800 illustrated in FIG. 8 and discussed above and will be discussed in that exemplary context.

Figure 11A:
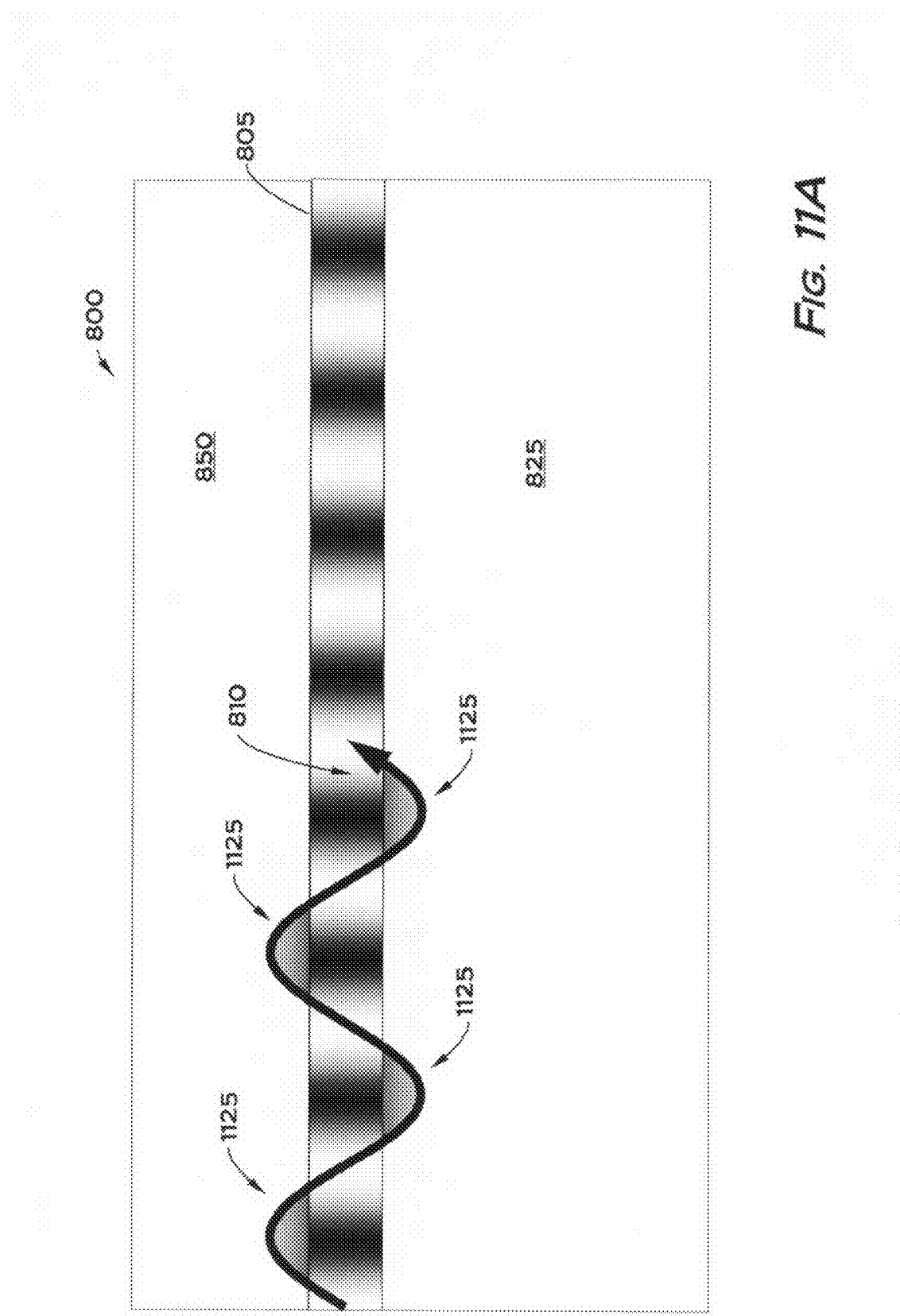

As illustrated in FIG. 11A, an evanescent field 1125 of the electromagnetic wave of light 810 extends beyond the optical waveguide core 805 and into the cladding 850 of the optical waveguide 800. The illustrated evanescent field 1125 can be viewed as an evanescent wave. As will be appreciated by those of ordinary skill in the art having benefit of this disclosure, the evanescent field 1125 can decay exponentially beyond the circumferential or lateral boundary of the optical waveguide core 805. For example, the evanescent field 1125 can have elevated intensity in regions of the substrate 825 and the cladding 850 disposed within a distance of the optical waveguide core 805 that is about one-third of the wavelength 975 of the electromagnetic wave of light 810. Accordingly, the evanescent field 1125 for a wavelength 975 can be viewed as extending beyond the optical waveguide core 805 about one-third of the wavelength 975.

FIG. 11B illustrates the cladding 850 comprising the optical material 100, which comprises polymeric material 1075 and gas-filled bubbles 1000 as discussed above. In certain exemplary embodiments, FIG. 11B illustrates the size of the gas-filled bubbles 1000 exaggerated relative to the width of the optical waveguide core 805. For example, the optical waveguide core 805 can have diameter or a lateral dimension of about 9.5 microns for carrying an electromagnetic wave of light 810 having wavelength 875 of about 1,550 nm (for single mode), and the gas-filled bubbles 1000 can have a diameter of less than about 1,550 nm, such as in a range of 50-500 nm.

In certain exemplary embodiments, the gas-filled bubbles 1000 can be sized such that one dimension, two dimensions, three dimensions, and/or every dimension of the gas-filled bubbles 1000 is about 0.01, 0.03, 0.05, 0.08, 0.1, 0.2, 0.3, 0.4, 0.5, 0.6, 0.7, 0.8, 0.9, or 1.0 times the wavelength 875 of the electromagnetic wave of light 810, or in a range between any two of these values, for example. In certain exemplary embodiments, the gas-filled bubbles 1000 may have a non-spherical shape or may be elongated.

In certain exemplary embodiments, a majority of the gas-filled bubbles 1000 that substantially interact with the evanescent field 1125 can be sized such that one dimension, two dimensions, three dimensions, and/or every dimension of the gas-filled bubbles 1000 is about 0.01, 0.03, 0.05, 0.08, 0.1, 0.2, 0.3, 0.4, 0.5, 0.6, 0.7, 0.8, 0.9, or 1.0 times the wavelength 875 of the electromagnetic wave of light 810, or in a range between any two of these values, for example.

In certain exemplary embodiments, a majority of the gas-filled bubbles 1000 that substantially interact with the evanescent field 1125 can be sized such that one dimension, two dimensions, three dimensions, and/or every dimension of the gas-filled bubbles 1000 is less than about 0.05, 0.06, 0.07, 0.08, 0.09, 0.1, 0.2, 0.3, 0.4, 0.5, 0.6, 0.7, 0.8, 0.9, or 1.0 times the evanescent field 1125 of the electromagnetic wave of light 810, or in a range between any two of these values, for example.

In certain exemplary embodiments, a fraction of the gas-filled bubbles 1000 that are disposed within about 99 percent of the evanescent field 1125 (or within a region that encompasses about 99 percent of the energy in the evanescent field 1125) can be sized such that one dimension, two dimensions, three dimensions, and/or every dimension of the gas-filled bubbles 1000 is about 0.01, 0.03, 0.05, 0.08, 0.1, 0.2, 0.3, 0.4, 0.5, 0.6, 0.7, 0.8, 0.9, or 1.0 times the wavelength 875 of the electromagnetic wave of light 810, or in a range between any two of these values. That fraction can be a statistical majority, at least 50 percent, at least 75 percent, at least 90 percent, or at least 95 percent, for example.

In certain exemplary embodiments, the largest dimension of each of the gas-filled bubbles 1000 can be less than about 50, 60, 75, 90, 100, 125, 150, 200, 250, 300, 350, 400, 500, 600, 800, or 1,000 nm or in a range between any two of these values, for example.

As illustrated in FIG. 11B, the evanescent field 1125 extends into the optical material 100 and thus has an opportunity to interact with the polymeric material 1075 and the gas-filled bubbles 1000 of the optical material 100. Dimensioned smaller than the wavelength 875, the gas-filled bubbles 1000 avoid causing excessive scattering loss of the electromagnetic wave of light 810.

Without being bound by theory, the evanescent field 1125 is believed to avoid deleterious scattering in similar manner to the scattering avoidance illustrated in FIG. 10 and discussed above. In other words, the evanescent field 1125 that extends into the optical material 100 can effectively bend around, bypass, or otherwise avoid obstruction by the individual gas-filled bubbles 1000. The electromagnetic wave of light 810 and its evanescent field 1125 effectively experience the gas-filled bubbles 1000 and the polymeric material 1075 as an integrated composite material rather than individually. In other words, the evanescent field 1125 interacts with the gas-filled bubbles 1000 on a macro scale, largely without being scattered by individual gas-filled bubbles 1000. The gas-filled bubbles 1000 can contribute to the refractive index of the optical material 850 without causing undue scattering loss. More specifically, the gas-filled bubbles 1000 can lower the refractive index of the optical material 100 substantially below the refractive index of the base, bubble-free polymeric material 1075 itself.

This effect can be viewed as conceptually analogous to how a naturally occurring crystal can have naturally occurring, atomic- or molecular-scale spaces between bonded elements without inducing excessive scattering of light propagating through the crystal. Such spaces can be too small to deflect individually or scatter a ray of light transmitting through the crystal, but nonetheless contribute collectively to the crystal's refractive index.

Light propagating through a medium comprising particles may undergo Mie scattering or Rayleigh scattering, each of which has theory and accompanying mathematical equations.

Without being bound by theory, sizing the gas-filled bubbles 1000 as taught herein is believed to avoid deleterious levels of Mie or Rayleigh scattering or some similar phenomenon associated with interaction between the evanescent field 1125 and the gas-filled bubbles 1000.

In certain exemplary embodiments, the gas-filled bubbles 1000 are randomly or uniformly dispersed throughout the optical material 100 and the cladding 850, or in a predetermined region thereof. In certain exemplary embodiments, the gas-filled bubbles 1000 are periodically distributed or distributed in a predetermined pattern throughout the optical material 100 and the cladding 850.

In certain exemplary embodiments, the gas-filled bubbles 1000 are concentrated near the optical waveguide core 805. Thus, the cladding 850 can have a higher concentration of the gas-filled bubbles 1000 near the optical waveguide core 805 than near the outer surface of the cladding 850. The concentration of gas-filled bubbles 1000 in the optical material 100 can vary as a function of lateral distance from the optical waveguide core 805. The number of gas-filled bubbles 1000 in a unit volume of the optical material 100 can vary according to, or be dependent upon, position within the cladding 850 and/or based on distance from the optical waveguide core 805.

In certain exemplary embodiments, the gas-filled bubbles 1000 are interconnected with one another, and/or gas can transfer or pass among gas-filled bubbles 1000. In certain exemplary embodiments, the gas-filled bubbles 1000 are substantially isolated from one another, for example to avoid communicating or transferring gas between or among individual gas-filled bubbles 1000. In certain exemplary embodiments, the optical material 100 comprises an open cell foam. In certain exemplary embodiments, the optical material 100 comprises a closed cell foam.

In certain exemplary embodiments, the optical material 100 comprises gas-filled bubbles 1150 that comprise a shell. The gas-filled bubbles 1150 may be lined with a layer or shell of glass, fused silica, silicate, or polymer, for example. In certain exemplary embodiments, the gas-filled bubbles 1150 can have a diameter in a range of 100 to 1,000 nanometers, for example. In certain exemplary embodiments, the gas-filled bubbles 1150 have a diameter in a range of about 10 to 100 nanometers. In certain exemplary embodiments, the gas-filled bubbles 1150 have a diameter in a range of about 50 to 250 nanometers. In certain exemplary embodiments, the gas-filled bubbles 1150 can comprise microballoons, for example. In certain exemplary embodiments, the gas-filled bubbles 1150 can comprise hollow glass nanobeads, for example. Sources for exemplary embodiments of the gas-filled bubbles 1150 (in particulate form) include Phosphorex, Inc. of Fall River, Mass.; Ekowool of Moscow, Russia; and Nanotechnology by of Hollandiastraat 5, 6006 TT Weert, The Netherlands. Additionally, those of ordinary skill in the art having benefit of this disclosure will be able to make optically transparent beads and spheres of glass, silica, and polymers that are hollow across the full range of dimensions specified in this paragraph without undue experimentation based on the various published methods described in readily accessible scientific literature. In certain exemplary embodiments, the gas-filled bubbles 1150 comprise hollow spheres of a fluoropolymer or an amorphous fluoropolymer.

In certain exemplary embodiments, the outer surface of the cladding 850 is coated with a material that is substantially free of any gas-filled bubbles 1000. For example, the cladding 850 can comprise an outer layer that substantially consists of the polymeric material 1075. Thus, the cladding 850 can comprise a plurality of layers, with the layer closest to the optical waveguide core 805 comprising gas-filled bubbles 1000. Such an inner layer can have a thickness of about 1, 5, 10, 15, or 20 microns, or a range between any two of these values. In certain exemplary embodiments, the inner layer has a thickness of about ten times the wavelength 975 of the electromagnetic wave of light 810. In certain exemplary embodiments, the inner layer has a thickness of at least two times the wavelength 975 of the electromagnetic wave of light 810. In certain exemplary embodiments, the inner layer 975 has a thickness of between about five and twenty times the wavelength 975 of the electromagnetic wave of light 810. In certain exemplary embodiments, the inner layer can have a thickness selected to substantially encase or envelop the evanescent field 1125. In certain exemplary embodiments, the inner layer can have a thickness that encases or envelops at least about 98 percent of the energy in the evanescent field 1125. In certain exemplary embodiments, the inner layer can have a thickness that is at least about two, three, four or five times the dimension of the evanescent field 1125 that extends laterally outside the optical waveguide core 805, or in a range between any two of these factors.

In certain exemplary embodiments, the gas-filled bubbles 1000 can have substantially common diameters or can be within a predefined range of values. In certain exemplary embodiments, the respective diameters of the gas-filled bubbles 1000 can vary as a function of distance from the optical waveguide core 805. For example, gas-filled bubbles 1000 that are close to the optical waveguide core 805 can be small relative to gas-filled bubbles 1000 that are farther from the optical waveguide core 805 or that are near the outer surface of the cladding 850.

In certain exemplary embodiments, the gas-filled bubbles 1000 can have a geometric form that can be characterized as round, rounded, disk-shaped, saucer-shaped, football-shaped, spherical, circular, oblong, stretched, distorted, elongated, elongate, dog-bone-shaped, dumbbell-shaped, cylindrical, elliptical, globe-shaped, pyramid-shaped, peanut-shaped, rod-shaped, diamond-shaped, ball-shaped, smooth, pointed, pointy, sharp, three-dimensional, indented, crescent, convex, protruding, doughnut-shaped, toroidal, branched, rotationally symmetric about one axis, rotationally symmetric about two axes, rotationally symmetric about three axes, or some other appropriate form, to mention a few examples.

In certain exemplary embodiments, the polymeric material 1075 can comprise (or consist of) one or more of the following materials, without limitation: a fluoropolymer; a perfluoropolymer; polymethylmethylacrate ("PMMA"); an amorphous fluoropolymer ("AF"); one of the products marketed by DuPont under the trade name TEFLON AF; one of the products marketed by Ashahi Glass under the trade name CYTOP; one of the optical polymers available from Ovation Polymers, Inc. of Medina, Ohio, such as the product marketed under the identifier "UV-OPTI-CLAD 1.33CM" that reportedly has a refractive index of about 1.33 and approaching that of water or the product marketed under the identifier "UV-OPTI-CLAD 1.34CM; a copolymer of tetrafluoroethylene ("TFE") with perfluoromethylvinylether, perfluoro-2-(2-fluorosulfonylethoxy)propyl vinyl ether, perfluoroethylvinylether, perfluoropropylene, perfluorodimethyldioxole, etc.; polytetrafluoroethylene ("PTFE"); perfluoroalkoxy ("PFA"); ethylene-tetrafluoroethylene ("ETFE"); a dipolymer of copolymerized units of tetrafluoroethylene and perfluoro(ethyl vinyl ether); fluorinated ethylene propylene ("FEP"); a copolymer of polymerized units of tetrafluoroethylene and perfluoro(ethyl vinyl ether); polymethylmethacrylate ("PMMA"); polyfluoro-methacrylate; polyvinyl fluoride ("PVF"); polyimide; cross-linked polyimide; fluorinated polyimide; cholofluorinated polyimide; fluorinated poly (arylene ether) ("FPAE"); benzocyclobutene; fluorinated benzocyclobutene; an electro optic polymer; an optical polymer; a thermoplastic that is substantially transparent; or some other appropriate polymer or plastic, for example.

In certain exemplary embodiments, an amorphous fluoropolymer is provided in a solvent for surface application. For example, the product marketed by DuPont under the trade name TEFLON AF is available from DuPont in a liquid form. (Similar products are available from other sources, such as those disclosed in the immediately preceding paragraph.) The liquid is applied to a surface. The solvent is driven off with heat, leaving a coating of amorphous fluoropolymer on the surface. In accordance with certain exemplary embodiments of the present invention, the gas-filled bubbles 1150 (in particulate form as hollow spheres or beads) are added to such a commercially available liquid. The liquid and gas-filled bubbles 1150 are applied to a surface, such as a waveguide core, and the solvent is removed by application of heat. The resulting combination of amorphous fluoropolymer and gas-filled bubbles 1150 can be heated to, towards, or beyond the melting point, softening point, or glass transition point of the amorphous fluoropolymer. Accordingly, the amorphous fluoropolymer can have an enhanced refractive index.

Turning now to FIG. 12, this figure illustrates a flowchart of an exemplary process 1200 for elevating refractive index of a material according to certain embodiments of the present invention. Process 1200, which is entitled Elevate Refractive Index, will be discussed with exemplary reference to the foregoing figures, without limitation.

Certain steps in process 1200, as well as in other processes and methods disclosed or taught herein, may naturally need to precede others for the present invention to function as described. However, the present invention is not limited to the order of the steps described if such order or sequence does not adversely alter the functionality of the present invention to the extent of rendering the invention inoperable or nonsensical. That is, it is recognized that some steps may be performed before or after other steps or in parallel with other steps without departing from the scope and spirit of the present invention.

In certain exemplary embodiments, process 1200 can be computer based. A computer system may control execution of process 1200 in whole or in part, for example.

At step 1205 of process 1200, particles are obtained that have a capability of liberating, producing, emitting, or generating gas in response to being heated or to decomposition. In accordance with certain exemplary embodiments, the particles can comprise or be a chemical blowing agent, as will be discussed below.

At step 1210, mechanical processing decreases the sizes (and masses) of the particles, thus reducing the amount of gas each liberates when heated. The particle sizes can be reduced via processing with a ball mill, a vibration mill, a pin mill, a fluid energy mill, a cutter mill, a jet mill, or a hammer mill, for example. In certain exemplary embodiments, the resulting average particle size can be about 0.5 microns. In certain exemplary embodiments, the average particle size can be in a range of about 0.1 to about 0.25 microns at this step, for example.

Representative processing equipment is available from Fluid Energy Processing and Equipment Company of Telford, Pa., for example. ICO, Inc. of Houston, Tex. and Powdersize, Inc. of Quakertown, Pa. are representative providers of relevant particle sizing services.

At step 1215, average particle size and/or average particle mass is further reduced. Processing the particles reduces the capacity of gas that each particle can liberate via a chemical reaction or degradation for example. In an exemplary embodiment, a portion of the particles' gas generation capacity is consumed by heating the particles under controlled conditions. The particles produce gas without exhausting their full potential. The particles can flow on an air feed into a heated zone where erosion or chemical reaction caused or initiated by heat occurs, for example. In an exemplary embodiment, an air stream flows the particles in front of a heating element or other device that transfers heat to the particles.

At step 1220, an instrument analyzes the particles to determine their size. For example, an air stream can feed a stream of the particles past an instrument that assesses size via laser diffraction, deep ultraviolet scattering, or x-ray scattering or diffraction. In one exemplary embodiment, the instrument comprises a system such as the Coulter LS230 Particle Size Analyzer that can detect particles in the range of 0.04-2,000 microns.

At step 1225, a computer system makes a determination about whether particles have an appropriate size. The computer system may comprise a general purpose computer running a program or a special purpose computer, for example. In certain exemplary embodiments, a programmable logic controller or a computer-based process control system executes step 1225 and/or other steps in process 1200. In certain exemplary embodiments, the computer can comprise a controller that may comprise an automatic control program or circuit. Such an automatic control program or circuit can may comprise a proportional plus integral ("PI") controller or a proportional plus integral plus derivative ("PID") controller for example. In various other exemplary embodiments, the controller can comprise a Kalman filter, a stochastic filter, a deadbeat controller, a multivariate controller, a least-squares computation, an anti-reset windup provision, a feed forward correction, a digital controller, an analog controller, fuzzy logic, cascaded control, microprocessor-based control, or some other effective control technology, feedback control loop, or appropriate automatic feedback control means, without limitation.

The computer system typically receives input from the instrument that detects particle size. The size or amount of material in each particle relates to its gas producing capacity, which in turn can relate to size of the gas-filled bubbles 1000. Accordingly, controlling particle size can control bubble size.

If the particles are larger than a threshold size and thus are expected to yield a bubble size larger another threshold size, then process 1200 loops back to step 1215 and iterates steps 1215 and 1225. Iteration continues until the particles are sized to produce a target amount of gas that would produce a desired bubble size or volume.

When execution of step 1225 results in a determination that the particles have an appropriate distribution of sizes for providing gas-filled bubbles 1000 having a specified distribution of sizes (for example within a predetermined range), then step 1230 executes. At step 1230, the appropriately sized particles are combined with the polymeric material 1075.

At step 1235, the combined polymeric material 1075 and particles are heated and applied to an optical surface, typically but not necessarily with the polymeric material 1075 in a molten state or melting. For example, the polymeric material 1075 and particles can be extruded over or manually dabbed on the surface 275 of the taper 220 illustrated in FIG. 2 and discussed above, the surface 325 illustrated in FIG. 3 and discussed above, the surface 425 illustrated in FIG. 4 and discussed above, the surface 525 illustrated in FIG. 5 and discussed above, a surface of a PLC, a core of an optical fiber to form a cladding, a cladding of an optical fiber to form a double clad optical fiber, a prism, or some other place that can benefit from optical characteristics imparted by the gas-filled bubbles 1000.

At step 1240, each particle produces gas that produces a gas-filled bubble 1000 as discussed above. With the polymeric material 1075 in a molten or softened state, the gas forms the gas-filled bubbles 1000, resulting in an exemplary embodiment of the optical material 100 as discussed above. The gas-filled bubbles 1000 typically are smaller than the wavelength 975 of the electromagnetic wave of light 810 that is to be managed. Process 1200 ends following step 1240, and the resulting optical system can be deployed.

Supplemental to the foregoing discussion of process 1200, various exemplary methods for forming the gas-filled bubbles 1000 can comprise mechanical, chemical, or physical processing. Mechanical processing can comprise whipping gas into the polymeric material 1075 or a polymer melt, a polymer solution, or a polymer suspension thereof. Hardening by catalytic action, heat, or a combination of catalytic action and heat can entrap the gas-filled bubbles 1000, for forming the optical material 100. Chemical processing can comprise thermally decomposing a chemical blowing agent to produce nitrogen, carbon dioxide, or another gas. The heat can be applied directly, or generated from exothermic heat of polymerization reaction. Physical processing can comprise reduction of system pressure to expand a gas that is dissolved in the polymeric material 1075, volatilization of a low-boiling liquid such as methylene chloride or a fluorocarbon, or adding hollow microspheres to the polymeric material 1075.

Physical blowing agents can include carbon dioxide, nitrogen, NOx, argon, xenon, krypton hydrocarbon, or water, for example. Physical blowing agents are typically gaseous in nature.

The physical blowing agent, which can be a fluid capable of becoming a gas under ambient conditions, is injected into a molten polymeric stream (e.g. of the polymeric material 1075) to form a mixture. The mixture is subjected to a pressure drop, causing the physical blowing agent to expand and form the gas-filled bubbles 1000 in the polymer. For example, exposure to atmospheric conditions can cause the physical blowing agent to gasify, thereby forming the gas-filled bubbles 1000 or cells in the polymer. Both open and closed cell foams may be produced depending on the conditions under which foaming occurs. Physical blowing agents provided in a supercritical fluid state in an extruder may also be employed, including supercritical carbon dioxide and supercritical nitrogen.

Some physical blowing agents include, but are not limited to, volatile organic compounds ("VOCs") including the light, aliphatic hydrocarbons such as the C3 to C5 hydrocarbons ("HCs") such as propane, n-butane, isobutane, butylene, isobutene, pentane, isopentane, cyclopentane, neopentane, hexane, and so forth, and other HCs including hexane and cyclohexane; methylene chloride; chlorofluorocarbons ("CFCs") such as trichlorofluoromethane (CFC-11); hydrochlorofluorocarbons ("HCFCs"); dialkyl ethers; alkyl alkanoates; aliphatic and cycloaliphatic hydrofluorocarbons; hydrochlorocarbons; fluorine-containing ethers; and so forth.

Chemical blowing agents often are low molecular weight organic compounds that decompose at a particular temperature and release a gas such as nitrogen, carbon dioxide, or carbon monoxide. Examples of chemical blowing agent can include sodium bicarbonate, citric acid, organic acid salts, azodicarbonamide, azobisformamide, azobisisobutyrolnitrile, diazoaminobenzene, 4,4'-oxybis(benzene sulfonyl hydrazide) ("OBSH"), N,N'-dinitrosopentamethyltetramine ("DNPA"), sodium borohydride, sodium bicarbonate/citric acid mixtures, citrate esters or mixtures with sodium bicarbonate, diazoaminobenzene (DAB), and other chemical blowing agent agents known in the art and combinations thereof.

A foaming agent may be used with an auxiliary foaming agent, nucleating agent, and/or a cross-linking agent. A nucleating agent can promote bubble formation and may comprise an inorganic particle, for example. Thus, nucleating agents may optionally be incorporated into a polymer melt to promote bubble nucleation. A nucleating agent is often a particulate of small size that may be added to and dispersed within a polymer melt. One class of nucleating agents comprises solid inorganic particles such as talc and calcium carbonate. U.S. Pat. Nos. 6,294,115 and 6,593,384 discuss cell nucleation in further detail and are hereby incorporated herein by reference.

For a chemically blown embodiment, bubble structures typically result from decomposition of the chemical blowing agent. The chemical blowing agent undergoes a chemical reaction in the polymeric material 1075, typically under conditions in which the polymeric material 1075 is molten, resulting in gas formation. In an extruder, high extruder pressure may dissolve the gas in the molten polymeric material 1075. Bubble nucleation may be optimized at the point of the polymeric material 1075 exiting the extruder die. A pressure drop associated with the molten polymer exiting the extruder die drop causes the gas to become super-saturated, resulting in nucleation of bubbles followed by bubble growth. Chilling the polymer rapidly freezes the bubbles as polymer viscosity increases. In certain embodiments, the optical material 100 can be extruded as a layer that is combined with other layers via coextrusion or other suitable process. For example, the optical material 100 can be extruded over a silica core of an optical fiber (the silica can be doped) to form a cladding with a protective polymer extruded over the cladding, in a coaxial arrangement.

Additional information for forming certain exemplary embodiments of the optical material 100 can be found in the following documents: 1) U.S. Pat. No. 6,555,590 entitled "Transparent Supermicrocellular Polymer Foams From High TG Polymers and Method for Manufacture" to Seng Tan, issued Apr. 29, 2003, the entire contents of which are hereby incorporated herein by reference; 2) U.S. Pat. No. 6,444,izo entitled "Method for Producing Crystalline Methacrylic Resin and Plastic Foam" to Mizumoto et al. issued Sep. 3, 2002, the entire contents of which are hereby incorporated herein by reference; 3) U.S. Patent Application Publication Number 2003/0008931 entitled "Expandable Polymeric Microspheres, Their Method of Production, and Uses and Products Thereof" to Soane et al. filed Sep. 5, 2002, the entire contents of which are hereby incorporated herein by reference; 4) U.S. Patent Application Publication Number 2002/0071947 entitled "Microcellular Foam and Foamed Composite Material" to Soane et al. filed Feb. 6, 2002, the entire contents of which are hereby incorporated herein by reference; 5) U.S. Pat. No. 6,617,364 entitled "Method for Synthesizing Thermo-Expandable Polymeric Microspheres" to Soane et al. filed Sep. 5, 2002, the entire contents of which are hereby incorporated herein by reference; 6) U.S. Pat. No. 6,638,984 entitled "Microcellular Foams, Their Method of Production, and Uses and Products Thereof" to Soane et al. filed Sep. 5, 2002, the entire contents of which are hereby incorporated herein by reference; 7) U.S. Pat. No. 6,709,870 entitled "Methods of Making Foamed Materials of Blended Thermoplastic Polymers Using Carbon Dioxide" to DeSimone et al., filed Mar. 1, 2000, the entire contents of which are hereby incorporated herein by reference; 8) U.S. Pat. No. 7,585,557 entitled "Foam Core Imaging Element with Gradient Density Core" to Aylward et al. filed Feb. 17, 2004, the entire contents of which are hereby incorporated herein by reference; and 9) U.S. Pat. No. 7,407,498 entitled "Construction of Medical Components Using Gas Assisted Microcellular Foaming to Olson filed Sep. 9, 2003, the entire contents of which are hereby incorporated herein by reference.

Turning now to FIGS. 13 and 14, FIG. 13 illustrates a functional block diagram of an exemplary light delivery system (embodied as a biomedical illumination system 1300 in this example) according to certain embodiments of the present invention. FIG. 14 illustrates a flowchart of an exemplary process 1400, entitled Compensate for Spectral Distortion, for compensating for spectral distortion associated with light scattering according to certain embodiments of the present invention. In an exemplary embodiment, process 1400 and the biomedical illumination system 1300 deliver light to biological material 1365 over one or more optical fibers with enhanced numerical aperture and compensate for any spectral variation associated with fiber optic transmission.

At step 1405 of process 1400, a light emitting diode ("LED") system 1305, or other appropriate light source or emitter of photons, produces light. In an exemplary embodiment, the light can be visible white light. A lens 1310 or other optic couples the light into a light-delivery optical fiber 1325, which may be a component of an endoscope, a flexible catheter, or a head-mounted illumination system, for example. As discussed above, in an exemplary embodiment, the light-delivery optical fiber 1325 comprises a cladding 850 (see FIG. 11B) comprising an optical material 100 that comprises gas-filled bubbles 1000 for enhancing numerical aperture. As discussed in further detail below, the LED system 1305 is part of a light supply 1308 that manipulates spectral content of the light to compensate for transmission effects.

At step 1410, the light delivery optical fiber 1325 guides the light to a system of light delivery optics 1335, such as one or more lenses, mirrors, optics, prisms, filters, or optical elements, for example. In certain exemplary embodiments, fiber optic transmission may vary spectral characteristics of the light, such as due to Mie or Rayleigh scattering associated with interaction with the gas-filled bubbles 1000. For example, lower-wavelength spectral components of the light may be attenuated. In certain exemplary embodiments, the gas-filled bubbles 1000 may collectively produce some diffraction that leads to some spectral distortion, for example. The light delivery system 1335 projects or otherwise couples the light to biological material 1365, such as tissue or an organ of a patient or research animal or specimen.

At step 1415, a distally located light-sampling interface 1340 couples to a feedback optical fiber 1330 a sample of the light that has transmitted over the light delivery optical fiber 1325. In an exemplary embodiment, the light-sampling interface 1340 can comprise a tap, splitter, coupler, or light pickup, for example. The feedback optical fiber 1330 transmits the sample to a spectrometer 1320.

At step 1420, the spectrometer 1320 spectrally analyzes the sample light, which is representative of illumination on the biological material 1365. For example, the spectrometer 1320 can determine intensity for a range of wavelengths of colors, such as across the visible light spectrum range. In an exemplary embodiment, the spectrometer 1320 generates an array of digital values spectrally representing the sample light and thus the light illuminating the biological material 1365. In addition to the spectrometer 1315 and the LED system 1305, the light supply 1308 comprises a controller 1315.

At step 1425, the controller 1315 compares a digitally represented spectrum of the sample light to a reference stored in a computer-readable memory. For example, the reference can be a digital representation of a spectrum of desired illumination. For example, a medical practitioner may desire illumination having a particular color, hue, shade, color temperature, whiteness, "LAB" reading, or chromaticity coordinates. In certain embodiments, multiple references will be stored so a medical practitioner can select and switch among multiple lighting conditions. In certain exemplary embodiments, the controller 1315 can comprise a computer, personal computer, special purpose computer, digital controller, embedded controller, or appropriate electrical circuit, for example.

At step 1430, the controller 1315 determines whether the spectrum of the sample light sufficiently matches the stored spectrum to provide the desired illumination characteristics at the biological material 1365. The controller 1315 can compare the sample and stored spectra, for example. If the sample light varies from the desired illumination characteristics within a threshold, then the controller 1315 deems that the LED system 1305 is providing acceptable lighting, and process 1400 loops back to step 1405. In this case, process 1400 continues from step 1405.

If, on the other hand, the sample light deviates unacceptably from the digitally stored representation of desired illumination, then step 1435 executes following step 1430. At step 1435, the controller 1315 takes corrective action and adjusts the LED system to provide light of desired spectral content at the biological material 1365. For example, the LED system 1305 can comprise individually controllable red, green, and blue LEDs. Adjusting the relative intensities of the light output from each of these LEDs can control spectral output of the light coupling into the light delivery optical fiber 1325 and thus the light illuminating the biological material 1365.

The controller 1315 can comprise an automatic control program or circuit for making spectral adjustments. Such an automatic control program or circuit can may comprise a PI controller or a PID controller for example. In various other exemplary embodiments, the controller 1315 can comprise a Kalman filter, a stochastic filter, a deadbeat controller, a multivariate controller, a least-squares computation, an anti-reset windup provision, a feed forward correction, a digital controller, an analog controller, fuzzy logic, cascaded control, microprocessor-based control, or some other effective color control technology, feedback control loop, or appropriate automatic feedback control means, without limitation.

Following execution of step 1435, process 1400 loops back to step 1405 and iterates. Accordingly, process 1400 continues illuminating the biological material 1365 with light of desired spectral content. Moreover, the controller 1320 refines the operation of the LED system 1305 to compensate for drift, aging, and other influences and changes.

Turning now to FIG. 15, this figure illustrates an exemplary optical system 1500 comprising layers 1515 of a first optical material interleaved between layers 1511 of a second optical material 100 that comprises polymeric material 1075 and gas-filled bubbles 1000 according to certain embodiments of the present invention. In an exemplary embodiment, the layers 1515 and the layers 1511 have different refractive indices and are arranged periodically to provide constructive and destructive interference of incident light. The differing refractive indices can result from having differing quantities of the gas-filled bubbles 1000 in the two layers 1515, 1511. In certain exemplary embodiments, the amount of gas-filled bubbles 1000 various sinusoidally across the optical system 1500. Accordingly, refractive index can vary smoothly and continuously or discretely and in a step-wise manner.

In certain exemplary embodiments, the layer 1515 has gas-filled bubbles of one diameter, and the layer 1511 has gas-filled bubbles of a different diameter. In certain exemplary embodiments, the sizes of the gas-filled bubbles 1000 varies sinusoidally across the optical system 1500. Accordingly, bubble diameters and/or volumes can vary smoothly and continuously or discretely and in a step-wise manner.

In certain exemplary embodiments, the optical system 1500 can filter light or reflect light of predefined wavelength. In certain exemplary embodiments, the optical system 1500 can comprise an interference filter or a thin-film interference filter. In certain exemplary embodiments, the optical system 1500 can comprise a Bragg reflector for stabilizing a laser. In certain exemplary embodiments, the optical system 1500 can be coated on an optical surface of an LED to facilitate transmitting light out of the LED or to manage or control light within the LED. In certain exemplary embodiments, the optical system 1500 can suppress reflection at an optical interface, such as between an LED surface and air or ambient gas.

Further descriptions of certain representative embodiments will now be discussed.

In accordance with certain exemplary embodiments of the present invention, a system operable to guide light of a wavelength along a path can comprise: a first optical material extending along the path and forming a waveguide core; and a second optical material adjoining the waveguide core and comprising: a polymeric material; and a large plurality of gas-filled bubbles, each substantially smaller than the wavelength, dispersed within the polymeric material. In certain embodiments of such a system, each of the gas-filled bubbles is substantially spherical with a diameter smaller than about one-half the wavelength, the polymeric material comprises a thermoplastic, and the light is visible light. In certain embodiments of such a system, the second optical material comprises a waveguide cladding circumscribing the waveguide core and operable to confine or bind the light substantially to the waveguide core, and the large plurality of gas-filled bubbles are substantially smaller than an evanescent field extending laterally into the waveguide cladding. In certain embodiments of such a system, each of the gas-filled bubbles comprises a bubble conforming to a selected size constraint, the polymeric material has a first refractive index at the wavelength, and the second optical material has a second refractive index at the wavelength that is substantially below the first refractive index as a result of the bubbles reducing refractive index in a substantial absence of undue scattering loss. Certain embodiments of such a system comprise: a flexible optical waveguide comprising the first optical material, the second optical material, a first end, and a second end; a light emitter, comprising optoelectronic material, coupled to the first end of the flexible optical waveguide, operable to emit the light in a visible spectral range for propagation from the first end towards the second end; an optical path leading from the second end to a detector, operable to convert a sample of the light to an electrical signal; and a controller, electrically coupled to the detector and to the light emitter, operable to compensate for scattering loss over the flexible optical waveguide via adjusting spectral output of the light according to the electrical signal. Certain embodiments of such a system further comprise an optical filter that is disposed along the path and that is operable to compensate for losses of the guided light due to the large plurality of bubbles scattering the light. In certain embodiments of such a system, a substantial amount of the large plurality of gas-filled bubbles are disposed for interaction with an evanescent field of the light, the first optical material comprises silicon dioxide or a glassy inorganic material, the second optical material circumscribes the waveguide core, the polymeric material comprises a fluoropolymer, and the system further comprises a protective coating applied over the second optical material.

In accordance with certain exemplary embodiments of the present invention, a method for fabricating an optical waveguide that is operable to convey light of a wavelength can comprise the steps of: forming a composition in response to adding particles to an optical polymer; coating at least a portion of an optical waveguide core with the composition; and forming bubbles in the optical polymer from respective ones of the added particles in response to heating the composition, a majority of the formed bubbles having a diameter that is significantly smaller than the wavelength at room temperature. In certain embodiments of such a method, forming bubbles in the optical polymer from respective ones of the added particles in response to heating the composition comprises decomposing the respective ones of the added particles to convert solid matter into gaseous matter. Certain embodiments of such a method can further comprise the step of in advance of adding the particles to the optical polymer, heating each of the particles to consume a portion of each particle's gas generation capacity. In certain embodiments of such a method the optical polymer comprises fluorine. In certain embodiments of such a method, each formed bubble is substantially spherical and is filled with one or more gasses, and an average of the diameters is less than about one-half the wavelength. In certain embodiments of such a method, the light is in a visible spectral range, and a substantial portion of the formed bubbles are disposed within two microns of the optical waveguide core.

In accordance with certain exemplary embodiments of the present invention, a method for making an optical fiber that guides light can comprise the steps of: providing a core having a first refractive index; and cladding the core with a composition that comprises: a base material having a second refractive index; and a sufficient quantity of gas-filled bubbles disposed adjacent the core to provide the composition with a third refractive index that is substantially below the first refractive index and the second refractive index, wherein the gas-filled bubbles are dimensioned not more than about one-half a wavelength of guided light. In certain embodiments of such a method the core has a substantially inorganic composition, the base material comprises a thermoplastic, a majority of the gas-filled bubbles comprise a first dimension, a second dimension, and a third dimension, with the first dimension substantially larger than the second dimension and the third dimension, and the first dimension is substantially smaller than about one-third of the wavelength. In certain embodiments of such a method, the step of cladding the core comprises: adding particles to the base material; melting the base material and liberating gas from each of the particles in response to heating the particles and the base material, the liberated gas forming the gas-filled bubbles. In certain embodiments of such a method, the cladding step comprises controlling bubble size to avoid undue scattering loss of the guided light in the made optical fiber, and each of the gas-filled bubbles comprises a shell distinct from the base material. In certain embodiments of such a method, cladding the core comprises forming the gas-filled bubbles substantially simultaneously with applying the base material to the core. In certain embodiments of such a method, cladding the core comprises forming the gas-filled bubbles prior to applying the base material to the core. In certain embodiments of such a method, cladding the core comprises forming the gas-filled bubbles in advance of applying the base material to the core.

In accordance with certain exemplary embodiments of the present invention, a method 5, for forming a totally internally reflective interface can comprise: providing particles that are operable to produce gas when heated; reducing respective gas production capacities of the particles in response to heating the particles so that each particle emits some gas; adding the reduced-capacity particles to an optical polymer; and forming the totally internally reflective interface in response to applying the optical polymer and the added particles to an optical element. In certain embodiments of such a method, forming the totally internally reflective interface further comprises forming voids in the optical polymer via applying heat to the optical polymer and the added reduced-capacity particles, the heat providing a molten phase of the optical polymer and causing the added reduced-capacity particles to emit gas and form bubbles in the optical polymer. In certain embodiments of such a method, the forming step comprises creating gas-filled voids in the optical polymer in a size range selected for reducing refractive index of the optical polymer while avoiding undue scattering loss for light having a wavelength in a range between about 350 and 2,000 nanometers.

In accordance with certain exemplary embodiments of the present invention, a method can comprise the steps of: inserting into mammalian tissue a catheter tip comprising: one or more optical fibers extending lengthwise; a channel extending lengthwise; and a diameter that is compatible with insertion into a human vascular lumen; feeding an indicator into the channel; exposing the mammalian tissue to the indicator; producing first light in response to illuminating the mammalian tissue and the indicator with second light transmitted over the one or more optical fibers; transmitting the produced first light over the one or more optical fibers; distinguishing the first light from the second light; and evaluating the mammalian tissue for a disease state in response to analyzing the transmitted first light. In certain embodiments of such a method, the first light comprises fluorescent light, and the evaluating step comprises assessing a reactive oxygen species present in the mammalian tissue according to intensity of the fluorescent light.

In accordance with certain exemplary embodiments of the present invention, an apparatus for conducting an assay of in vivo tissue can comprise: one or more optical fibers comprising: a proximal end that is operable to receive first light from a light source and to emit second light to a light detector; and a distal end that is operable to emit the received first light into the tissue and to receive the second light from the tissue; a channel, extending lengthwise alongside the one or more optical fibers, that is operable to deliver to the tissue a fluid that is operable to change the second light according to composition of the tissue; and a covering extending lengthwise and circumferentially surrounding the one or more optical fibers and the channel. In certain exemplary embodiments of such a system, the fluid comprises a fluorescent probe operable to detect presence in the tissue of one or more of a reactive oxygen species, superoxide, or a hydroxyl radical.

In accordance with certain exemplary embodiments of the present invention, a method for imaging atherosclerotic plaque in a vascular lumen can comprise the steps of: applying to the atherosclerotic plaque an agent that changes spectrally according to a parameter of the atherosclerotic plaque; coupling light to and from the applied agent over one or more optical fibers disposed in the vascular lumen; and spatially assessing the parameter of the atherosclerotic plaque in response to analyzing light transmitted over the one or more optical fibers. In certain embodiments of such a method, the parameter comprises vulnerability to rupture. In certain embodiments of such a method, spatially assessing the parameter comprises determining circumferential distribution in the vascular lumen of a biochemical that the atherosclerotic plaque comprises. In certain embodiments of such a method, the parameter comprises a reactive oxygen species, superoxide, or hydroxyl radical. In certain embodiments of such a method, the agent comprises a fluorescent probe that responds to one or more reactive oxygen species.

Technology useful for managing light has been described. From the description, it will be appreciated that an embodiment of the present invention overcomes limitations of the prior art. Those skilled in the art will appreciate that the present invention is not limited to any specifically discussed application or implementation and that the embodiments described herein are illustrative and not restrictive. Furthermore, the particular features, structures or characteristics that are disclosed may be combined in any suitable manner in one or more embodiments based on this disclosure and ordinary skill. Those of ordinary skill having benefit of this disclosure can make, use, and practice a wide range of embodiments via combining the disclosed features and elements in many permutations without undue experimentation. This disclosure not only includes the illustrated and described embodiments, but also provides a rich and detailed roadmap for creating many additional embodiments using the various disclosed technologies, elements, features, and their equivalents. From the description of the exemplary embodiments, equivalents of the elements shown herein will suggest themselves to those skilled in the art, and ways of constructing other embodiments of the present invention will appear to practitioners of the art. Therefore, the scope of the present invention is to be limited only by the accompanying claims.

What is claimed is:

1. A method, for fabricating an optical waveguide that is operable to convey light of a wavelength, comprising the steps of:
    heating each particle to be added to an optical polymer to consume a portion of each particle's gas generation capacity;
    forming a composition in response to adding particles to the optical polymer;
    coating at least a portion of an optical waveguide core with the composition; and
    forming bubbles in the optical polymer from respective ones of the added particles in response to heating the composition, a majority of the formed bubbles having a diameter that is significantly smaller than the wavelength at room temperature.

2. The method of claim 1, wherein forming bubbles in the optical polymer from respective ones of the added particles in response to heating the composition comprises decomposing the respective ones of the added particles to convert solid matter into gaseous matter.

3. The method of claim 1, wherein the optical polymer comprises fluorine.

4. The method of claim 1, wherein each formed bubble is substantially spherical and is filled with one or more gasses, and
    wherein an average of the diameters is less than about one-half the wavelength.

5. The method of claim 1, wherein the light is in a visible spectral range, and
    wherein a substantial portion of the formed bubbles are disposed within two microns of the optical waveguide core.

6. A method, for making an optical fiber that guides light, comprising the steps of:
    providing a core having a first refractive index, wherein the core has a substantially inorganic composition; and
    cladding the core with a composition that comprises:
        a base material having a second refractive index, wherein the base material comprises a thermoplastic; and
        a sufficient quantity of gas-filled bubbles disposed adjacent the core to provide the composition with a third refractive index that is substantially below the first refractive index and the second refractive index, wherein a majority of the gas-filled bubbles comprise a first dimension, a second dimension, and a third dimension, with the first dimension being substantially larger than the second dimension and the third dimension,
    wherein the gas-filled bubbles are dimensioned not more than about one-half a wavelength of guided light and the first dimension is substantially smaller than about one-third of the wavelength.

7. The method of claim 6, wherein the step of cladding the core comprises:
    adding particles to the base material;
    melting the base material and liberating gas from each of the particles in response to heating the particles and the base material, the liberated gas forming the gas-filled bubbles.

8. The method of claim 6, wherein the cladding step comprises controlling bubble size to avoid undue scattering loss of the guided light in the made optical fiber, and wherein each of the gas-filled bubbles comprises a shell distinct from the base material.

9. The method of claim 6, wherein cladding the core comprises forming the gas-filled bubbles substantially simultaneously with applying the base material to the core.

10. The method of claim 6, wherein cladding the core comprises forming the gas filled bubbles prior to applying the base material to the core.

11. The method of claim 6, wherein cladding the core comprises forming the gas-filled bubbles in advance of applying the base material to the core.

* * * * *